(12) United States Patent
Pratt et al.

(10) Patent No.: US 11,775,550 B2
(45) Date of Patent: Oct. 3, 2023

(54) SYSTEM FOR TRANSFORMATION OF DATA STRUCTURES TO MAINTAIN DATA ATTRIBUTE EQUIVALENCY IN DIAGNOSTIC DATABASES

(71) Applicant: Premier Healthcare Solutions, Inc., Charlotte, NC (US)

(72) Inventors: Katelyn A. Pratt, Fort Mill, SC (US); Michael P. Korvink, Waxhaw, NC (US)

(73) Assignee: PREMIER HEALTHCARE SOLUTIONS, INC., Charlotte, NC (US)

( * ) Notice: Subject to any disclaimer, the term of this patent is extended or adjusted under 35 U.S.C. 154(b) by 1178 days.

(21) Appl. No.: 16/159,475

(22) Filed: Oct. 12, 2018

(65) Prior Publication Data
US 2020/0117746 A1 Apr. 16, 2020

(51) Int. Cl.
*G16H 10/60* (2018.01)
*G06F 16/25* (2019.01)
*G16H 15/00* (2018.01)
*G06F 16/21* (2019.01)
*G16B 50/00* (2019.01)

(52) U.S. Cl.
CPC .......... *G06F 16/258* (2019.01); *G06F 16/214* (2019.01); *G16B 50/00* (2019.02); *G16H 10/60* (2018.01); *G16H 15/00* (2018.01)

(58) Field of Classification Search
None
See application file for complete search history.

(56) References Cited

U.S. PATENT DOCUMENTS

| | | | | |
|---|---|---|---|---|
| 8,447,760 | B1 * | 5/2013 | Tong | G06F 16/355 707/728 |
| 2006/0026156 | A1 * | 2/2006 | Zuleba | G06F 21/6227 707/999.005 |
| 2008/0201172 | A1 * | 8/2008 | McNamar | G16H 10/60 600/300 |
| 2011/0119089 | A1 * | 5/2011 | Carlisle | G06Q 10/06 705/3 |
| 2014/0164564 | A1 * | 6/2014 | Hoofnagle | H04L 67/125 709/217 |
| 2015/0025913 | A1 * | 1/2015 | Friedlander | G16H 10/60 705/3 |
| 2016/0371375 | A1 * | 12/2016 | Sasidhar | G06F 16/248 |
| 2019/0279749 | A1 * | 9/2019 | Wu | G06F 16/24578 |

* cited by examiner

*Primary Examiner* — Xuyang Xia
(74) *Attorney, Agent, or Firm* — Moore & Van Allen PLLC

(57) ABSTRACT

The invention provides a comprehensive data transformation system, method and computer program product structured for transformation of data structures to maintain data attribute equivalency in diagnostic databases. In some embodiments, the present invention is configured to determine a first source data structure based on at least received user information. The source data structure is typically comprises a comprising a first coding type. In addition, the present invention is configured to determine one or more source attributes associated with the first source data structure. Moreover, the present invention is configured for transforming the first source data structure to a first target data structure of a second coding type such that one or more target attributes associated with the first target data structure are equivalent to the one or more source attributes.

20 Claims, 7 Drawing Sheets

400B

SYSTEM FOR TRANSFORMATION OF DATA STRUCTURES TO MAINTAIN DATA ATTRIBUTE EQUIVALENCY IN DIAGNOSTIC DATABASES

FIELD OF THE INVENTION

The present invention embraces a system, computer program product, and method for transforming and mapping data structures across a plurality of distinct databases, based on at least data attributes of the data structures in diagnostic databases. The transformation of a first data structure of a first type of coding from a first database to map to a second data structure of a second type of coding in a second database is configured such that equivalence of the attributes of the first data structure is maintained after transformation to the second type of coding.

BACKGROUND

A conventional diagnostic database typically comprises data structures of a particular first type and associated attributes of each the data structures. For instance, the first type of data structures may comprise a first coding system. However, in some instances, analysis of these first type of data structures having a first type of coding requires transforming the first type of data structures to a second type of data structures comprising a second type of coding. However, conventional databases are neither configured to, nor are capable of, mapping/transforming the first type of data structure having the first type of coding to the second type of data structure having the second type of coding at all, much less transforming the data structure such that equivalence of data attributes of the data structures are maintained after the transformation. Moreover, conventional databases are further incapable of incorporating/integrating a data attributes of a third data structure into the foregoing transformation. Accordingly, there is a need for an advanced systems that addresses the above technical problems in existing systems. The advanced technical database processing and data structure transformation of the present invention ameliorates the foregoing deficiencies of conventional database technology, and also provides several advantages and improvements.

BRIEF SUMMARY

The following presents a simplified summary of one or more embodiments of the invention in order to provide a basic understanding of such embodiments. This summary is not an extensive overview of all contemplated embodiments, and is intended to neither identify key or critical elements of all embodiments, nor delineate the scope of any or all embodiments. Its sole purpose is to present some concepts of one or more embodiments in a simplified form as a prelude to the more detailed description that is presented later.

Embodiments of the present invention provide a system, computer program product, and a computer-implemented method for transformation of data structures to maintain data attribute equivalency in diagnostic databases. The technical system of the invention typically comprises a first database, wherein the first database comprises a plurality of source data structures associated with a first coding type. The technical system further comprises a second database, wherein the second database comprises a plurality of target data structures associated with a second coding type. The system further comprises a computer apparatus including at least one processor, at least one memory device with computer-readable program code stored thereon and a network communication device. The at least one processor is operatively coupled to the least one memory device and the network communication device such that the processing device is configured to execute the computer-readable program. In some embodiments, the invention is structured to receive a feature data structure, wherein the feature data structure comprises user information associated with a first user; based on at least the user information, determine a first source data structure of the plurality of source data structures of the first database, wherein the first source data structure comprises the first coding type; determine one or more source attributes associated with the first source data structure; transform the first source data structure to a first target data structure of the plurality of target data structures of the second database such that (i) the first target data structure comprises the second coding type, and (ii) one or more target attributes associated with the first target data structure are equivalent to the one or more source attributes associated with the first source data structure; and initiate, via a user interface, a presentation of the first target data structure on a display device associated with a user device.

In some embodiments, or in combination with any of the previous embodiments, the first coding type is an ICD-10 based code and the second coding type is an ICD-9 based code.

In some embodiments, or in combination with any of the previous embodiments, is invention is further configured to retrieve visit information associated with the first user, wherein visit information comprises one or more patient attributes.

In some embodiments, or in combination with any of the previous embodiments, the invention is configured to determine one or more probable target data structures of the plurality of target data structures of the second database associated with the first source data structure based on at least the visit information and the user information, wherein each of the one or more probable target data structures comprise the second coding type. Typically, the one or more probable target data structures may be determined based on determining an inpatient principal diagnosis code, an inpatient other ICD code, an outpatient principal diagnosis code and/or an outpatient other diagnosis code.

In some embodiments, or in combination with any of the previous embodiments, the invention is configured to determine one or more probable target data structures of the plurality of target data structures of the second database associated with the first source data structure based on at least the visit information and the user information, wherein each of the one or more probable target data structures comprise the second coding type, wherein the one or more probable target data structures comprise the first target data structure. The invention is further configured to determine, for each of the one or more probable target data structures, a probability of class for the first source data structure. Typically, transforming the first source data structure to the first target data structure may comprise mapping the first source data structure to the first target data structure of the one or more probable target data structures based on determining that the first target data structure comprises a highest probability of class.

In some embodiments, or in combination with any of the previous embodiments, the visit information comprises one or more patient attributes selected from a group comprising a patient type, a patient class, a point of origin, an admit type, a discharge status and/or MS-DRG data.

In some embodiments, or in combination with any of the previous embodiments, the first source data structure is associated with a first ICD code of the first coding type, wherein one or more source attributes comprise an ICD type, an ICD class, a rank and/or a Present on Admission (POA) indicator.

In some embodiments, or in combination with any of the previous embodiments, the first target data structure is associated with a first ICD code of the second coding type, wherein one or more target attributes comprise an ICD type, an ICD class, a rank and/or a Present on Admission (POA) indicator.

In some embodiments, or in combination with any of the previous embodiments, the invention is configured determine whether a discharge patient attribute associated with the first user succeeds a predetermined time interval; and transform the first source data structure to the first target data structure based on at least determining that the discharge patient attribute associated with the first user succeeds a predetermined time interval.

In some embodiments, or in combination with any of the previous embodiments, one or more of the databases are medical databases.

In some embodiments, or in combination with any of the previous embodiments, the invention is configured determine whether a discharge patient attribute associated with a second user succeeds a predetermined time interval; and retrieve a second target data structure of the plurality of target data structures of the second database, based on at least determining that the discharge patient attribute associated with the first user precedes a predetermined time interval.

The features, functions, and advantages that have been discussed may be achieved independently in various embodiments of the present invention or may be combined with yet other embodiments, further details of which can be seen with reference to the following description and drawings.

BRIEF DESCRIPTION OF THE DRAWINGS

Figure 1:
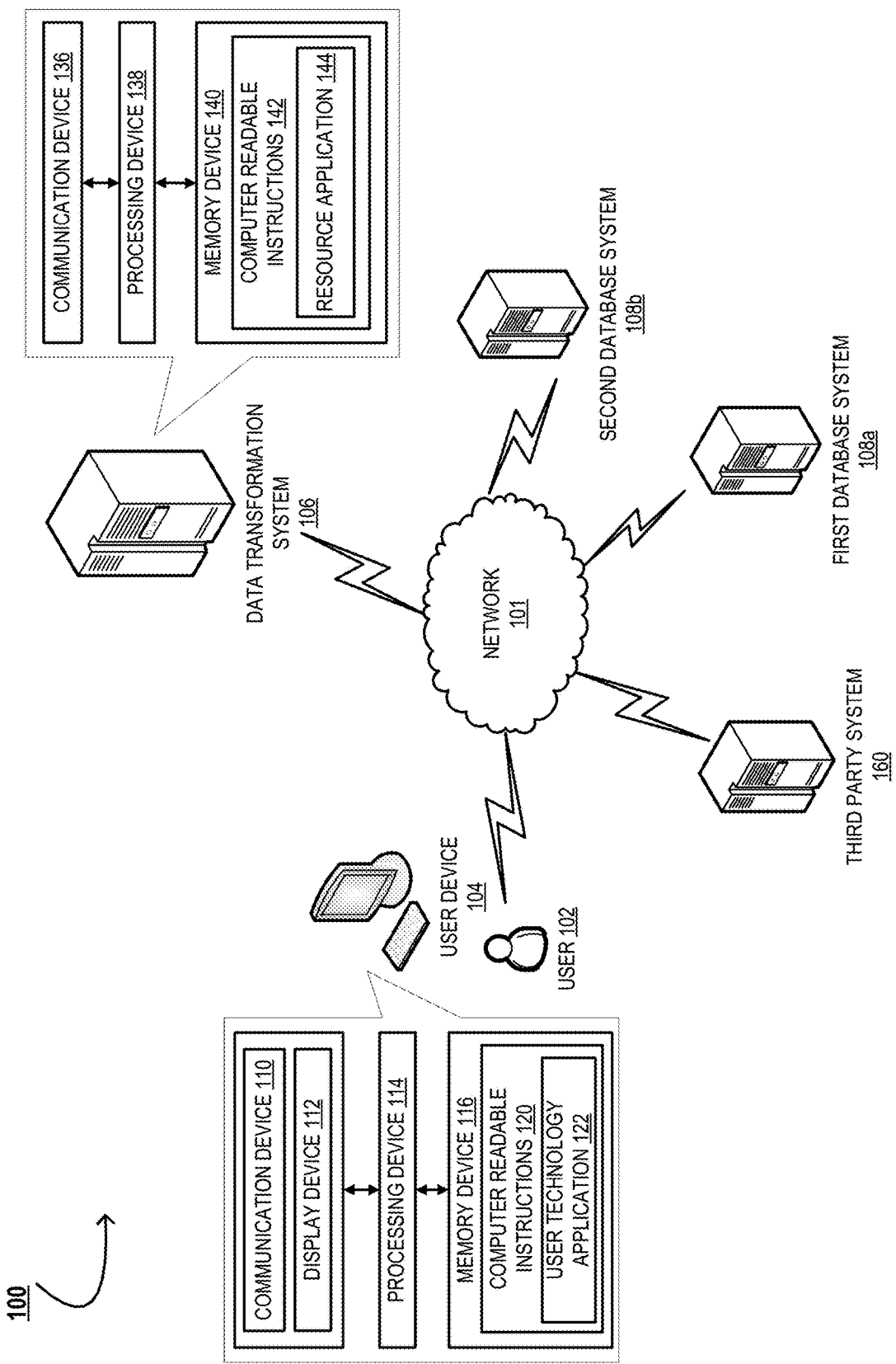
Figure 2:
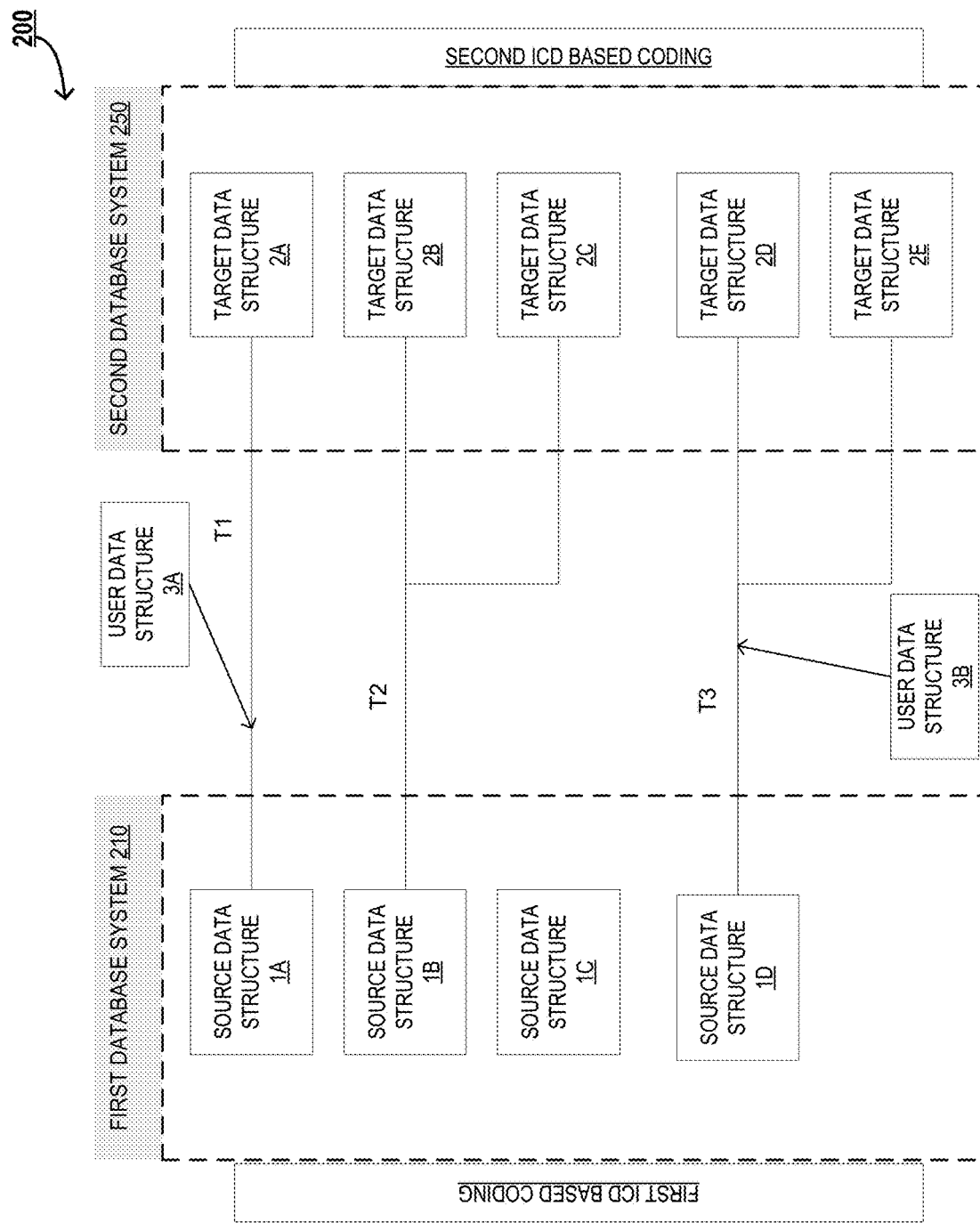
Figure 3:
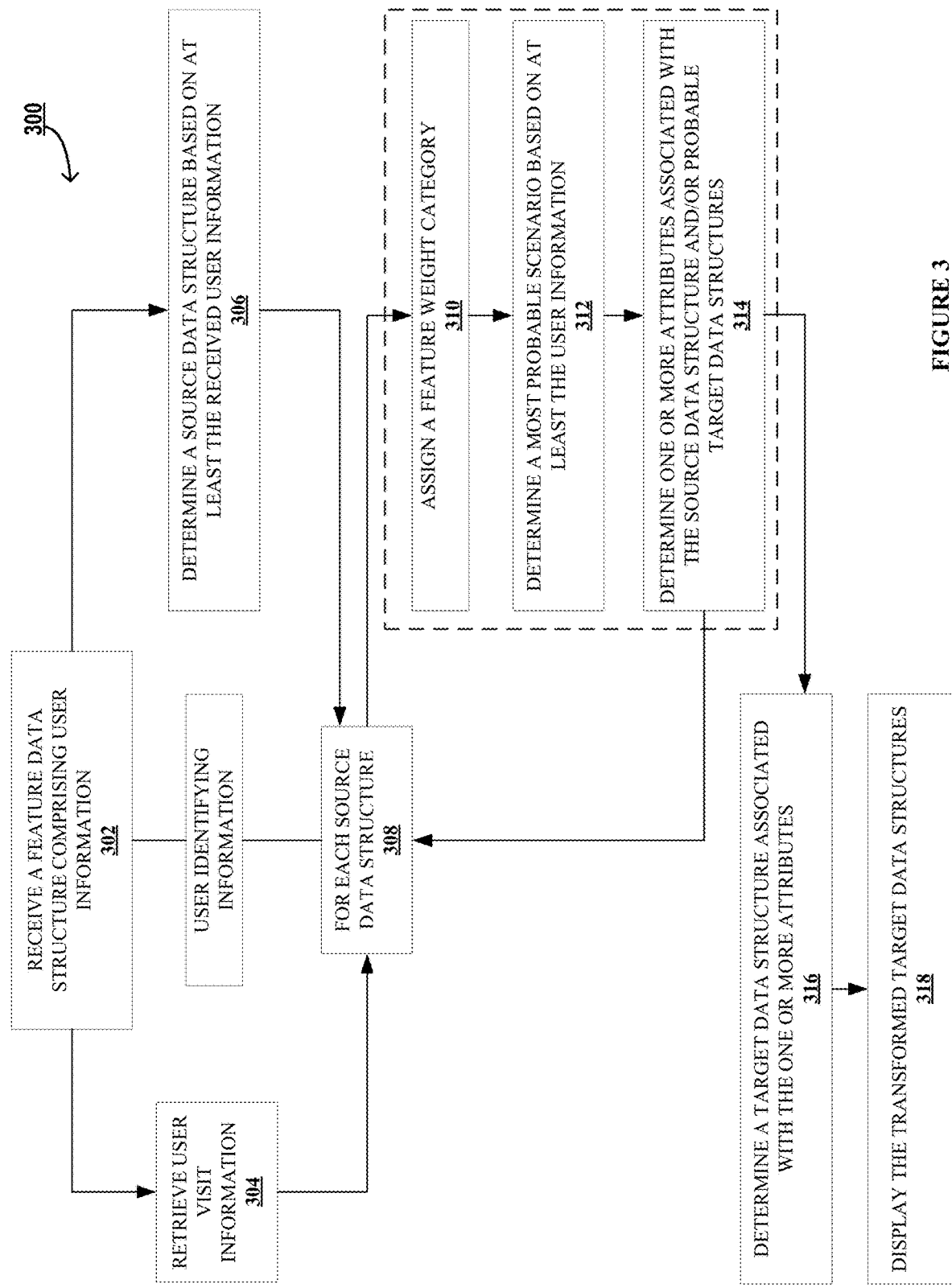
Figure 4A:
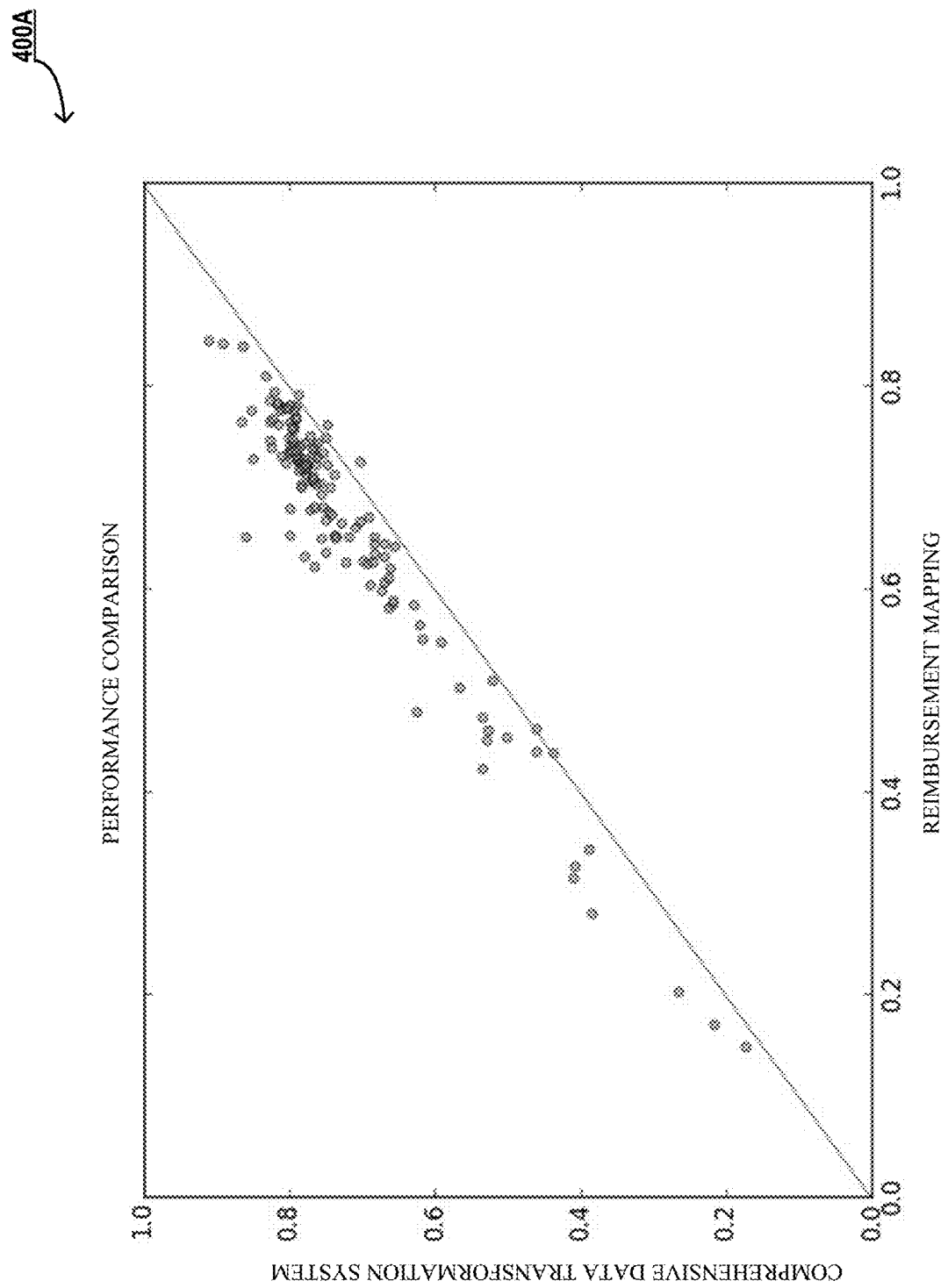
Figure 4B:
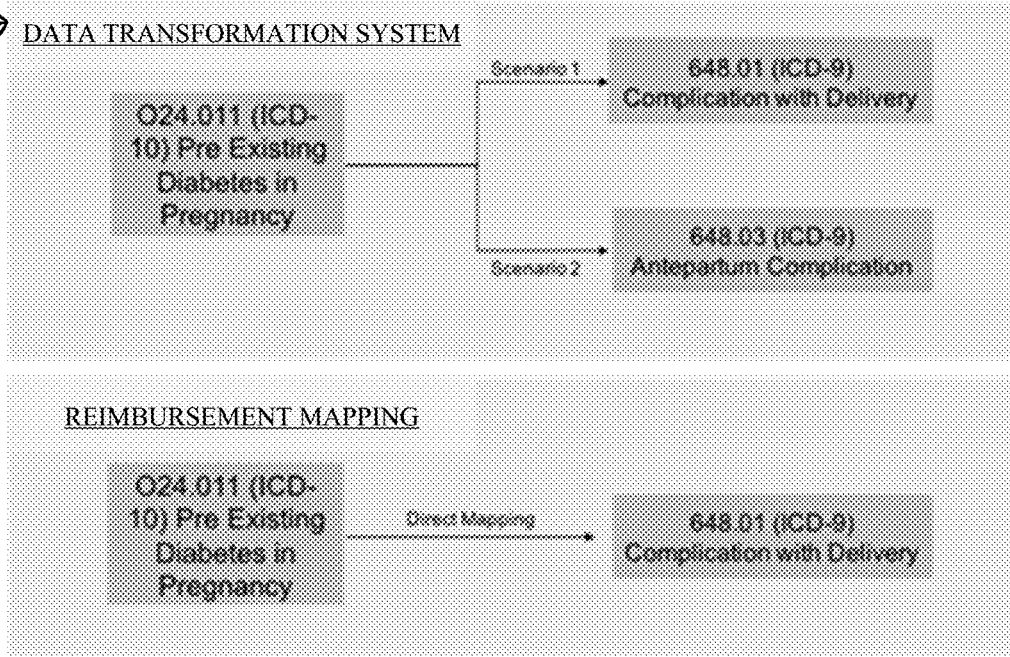
Figure 4B:
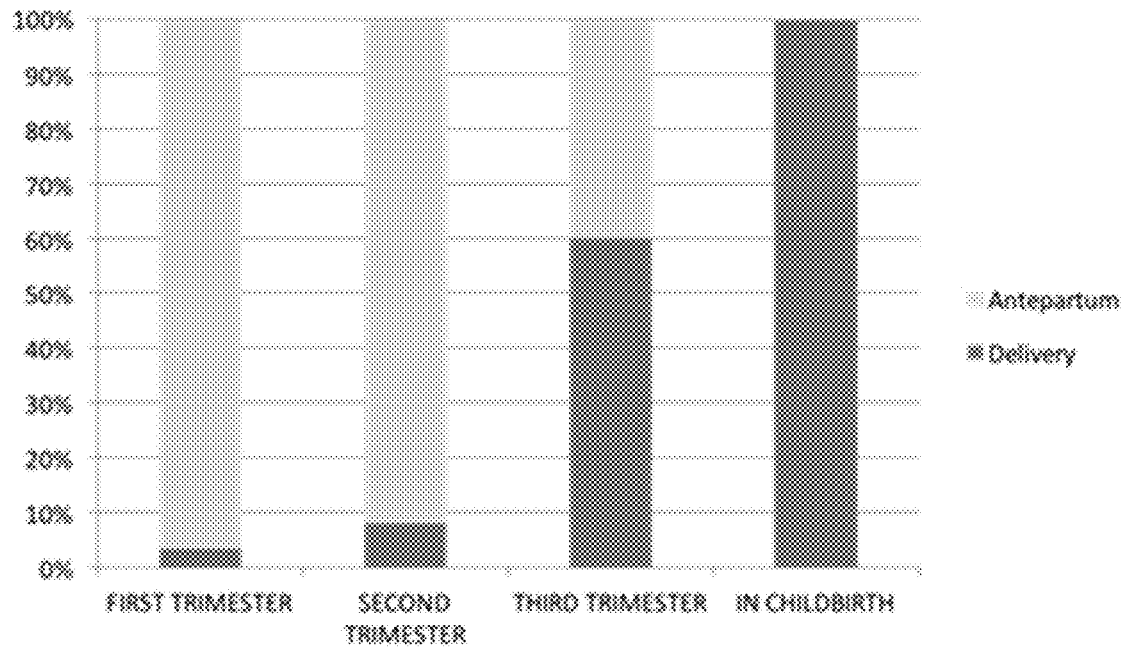
Figure 4C:
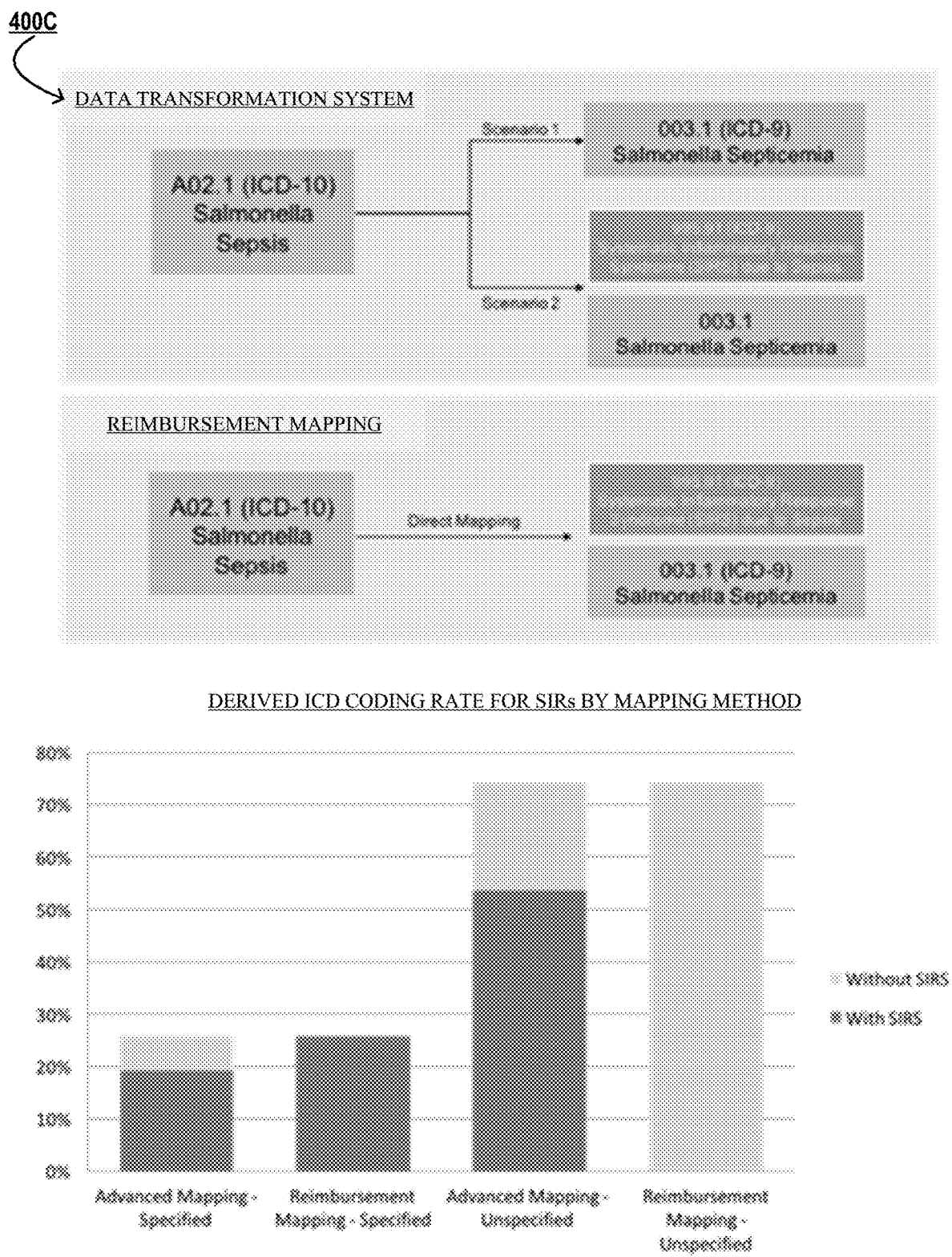
Figure 4D:
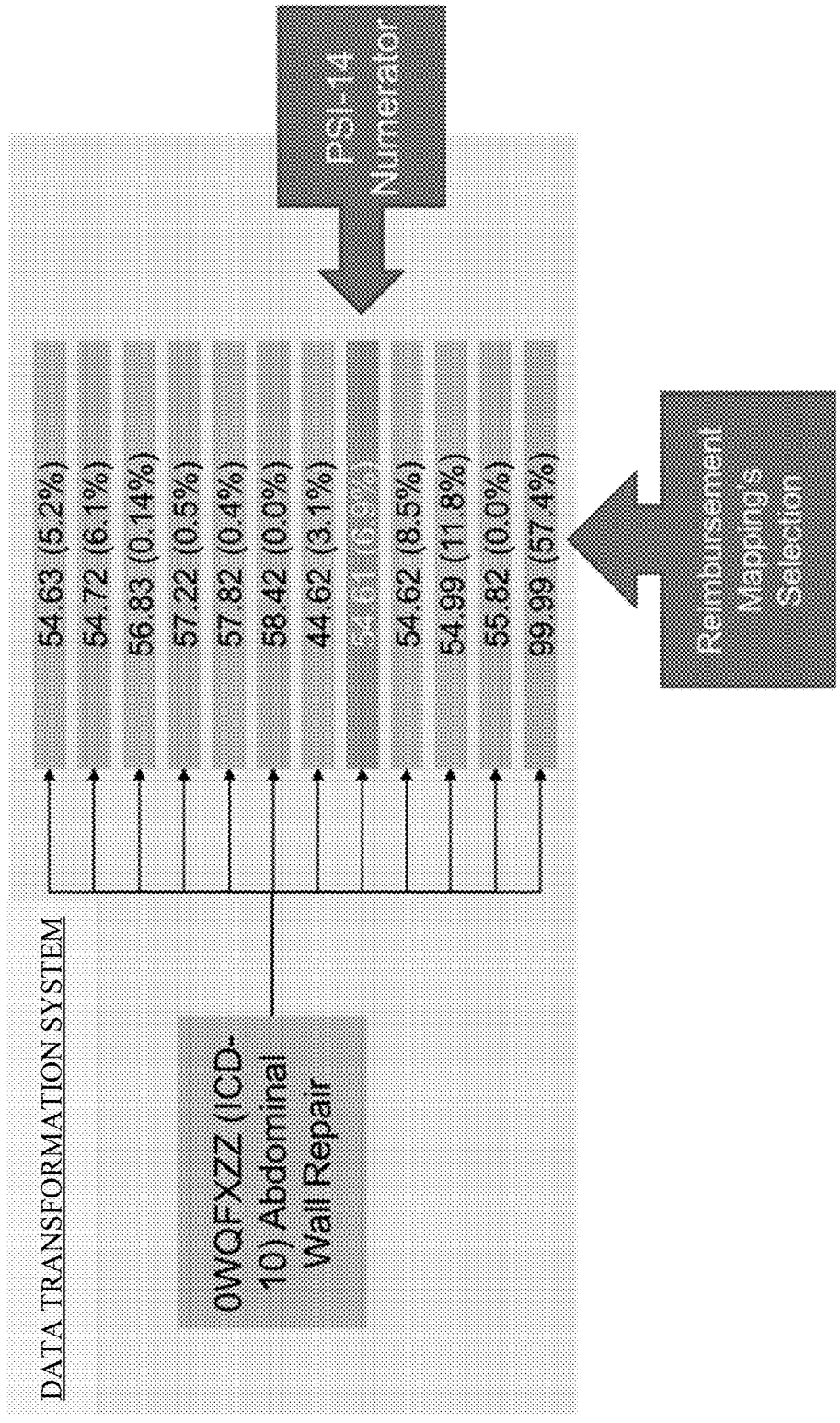

Having thus described embodiments of the invention in general terms, reference will now be made to the accompanying drawings, wherein:

FIG. 1 illustrates a comprehensive data transformation system environment 100, in accordance with some embodiments of the present invention;

FIG. 2 illustrates a high level schematic representation 200 of data transformation across database systems of different data structure types, in accordance with some embodiments of the invention;

FIG. 3 illustrates a high level process flow 300 for data transformation across database systems of different data structure types, in accordance with some embodiments of the invention;

FIG. 4A illustrates, a user Jaccard Coefficient Performance improvement, in accordance with some embodiments of the invention;

FIG. 4B illustrates, Pre-existing Diabetes in Pregnancy within the comprehensive data transformation system of the present invention and Reimbursement Mapping, in accordance with some embodiments of the invention;

FIG. 4C illustrates, Salmonella Sepsis within the comprehensive data transformation system of the present invention and Reimbursement Mapping, in accordance with some embodiments of the invention; and FIG. 4D illustrates, Post-Operative Wound Dehiscence Coding, in accordance with some embodiments of the invention.

DETAILED DESCRIPTION OF EMBODIMENTS OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to elements throughout. Where possible, any terms expressed in the singular form herein are meant to also include the plural form and vice versa, unless explicitly stated otherwise. Also, as used herein, the term "a" and/or "an" shall mean "one or more," even though the phrase "one or more" is also used herein.

In some embodiments, an "entity" or "enterprise" as used herein may be any institution employing information technology resources and particularly technology infrastructure configured for storing, analyzing a processing diagnostic and medical databases. In some instances, the entity's is associated with a first database storing a plurality of first type of data structures/source data structures, a second database may storing a plurality of second type of data structures/target data structures and/or the like. Although listed as a first and second database, it is understood that the first and second databases may be incorporated as distinct devices/systems or on a same device/system. Typically, these technology activities across multiple distributed technology platforms involve large scale processing of technology activity files and electronic records. As such, the entity may be any institution, group, association, hospital, medical research facility, financial institution, insurance provider, federal entity, establishment, company, union, authority or the like, employing diagnostic and medical data. In some embodiments, "entity" may refer to an individual or an organization that owns, operates and/or is otherwise associated with a system of networked computing devices and/or systems on which the comprehensive data transformation system of the present invention is implemented. The entity may be a business organization, a non-profit organization, a government organization, and the like. In other embodiments, the entity may be a single individual who wishes to log data and complex interactions amongst the data structures and ICD codes.

"Computing system", "computing device," "server" or "system" as used herein may refer to a networked computing device within the entity system environment or entity system infrastructure (e.g., a system structured for transformation of data structures to maintain data attribute equivalency in medical diagnostic databases, etc.). The computing system may include one or more of a processor, a non-transitory storage medium, a communications device, and a display. The computing system may support user logins and inputs from any combination of similar or disparate devices. Accordingly, in some embodiments, the computing system may be, may comprise or may be associated with a portable electronic device such as a smartphone, tablet, or laptop, or the computing system may be a stationary unit such as a personal desktop computer, networked terminal, or server. In some embodiments, the computing system may be a local or remote server which is configured to send and/or receive inputs from other computing systems on the network. Furthermore, as used herein the term "user device" or "mobile device" may refer to computing devices such as mobile phones, personal computing devices, tablet computers, wearable devices, and/or any portable electronic device capable of receiving and/or storing data therein.

A "medical diagnostic database," "diagnostic database," "first database" or "second database" as used herein, typically refers to a database that is configured to store a plurality of data structures (e.g., source type data structures or target type data structures described below). The database may be a relational database, a graph structured database, and/or the like.

A "data structure" is a record, node, or other database element which comprises a particular ICD based coding. The data structures may be structured to include a pointer to one or more data structures. In general, in some embodiments, each data structure comprises one or more properties/attributes, i.e., data/information regarding the particular ICD based coding. This data structure may be directed to describing, recording, identifying and/or documenting the particular ICD based coding. Although referred to as "a data structure", it is understood that, in some embodiments each particular ICD based coding may be associated with multiple data structures.

"Relationship" or "mapping," as used herein may refer to transformation of a first type of data structure having a first ICD based coding to one or more second types of data structures having a second ICD based coding, typically while still maintaining equivalence of the attributes of the data structures. In some embodiments, transforming comprises constructing a relationship mapping structure that links the first type of data structure to each of the associated one or more second types of data structures. In some embodiments, the relationship has a source data structure and a target data structure (described below), and is structured to indicate attributes of the relationship between the data structures (e.g., how the data structures are related, what properties of the data structures are integrated/connected, and/or the like).

"Property" or "attribute" or "technology element" as used herein may refer to a germane information of associated data structures, relationships, and other properties. As such properties may comprise diagnosis information (e.g., type of infection, infraction, condition, abnormalities, etc.), applicable general categories of conditions, physiological parameters/symptoms (e.g., organ/part of body affected), and/or the like associated with the relevant particular ICD based code. Data structures or attributes may be created as groups of sets organized by common properties, in which data structures, and attributes that have the same property belong to the same set. The data structures, and attributes may comprise descriptive data, textual data, unformatted data, formatted data, or any other available forms of data/information or a combination of forms. This data may be transformed, formatted, encoded, decoded, or otherwise fundamentally altered during storage, retrieval, data/language processing, and other operations.

As described herein, a "user" is an individual associated with an entity. In some embodiments, a "user" may be an employee (e.g., an associate, a project manager, an IT specialist, a manager, an administrator, an internal operations analyst, or the like) of the entity or enterprises affiliated with the entity, capable of operating the systems described herein. In some embodiments, a "user" may be any individual, entity or system who has a relationship with the entity, such as a customer. In other embodiments, a user may be a system performing one or more tasks described herein. "User" as used herein may refer to an individual who may utilize the comprehensive data transformation/mapping system. The user may be an agent, administrator, or employee of the entity who has authorization to add, modify, or delete data, or query existing data, data structures and/or relationships. In other embodiments, the user may be a client or customer of the entity. In yet other embodiments, the user may be unaffiliated with the entity who has some type of interaction with the entity's system. In some embodiments, the user may be a patient whose user information is being integrated with or is a basis for the transformation of the transformation of a first type of data structure having a first ICD based coding to one or more second types of data structures having a second ICD based coding. In some embodiments, a user may be any individual or entity who has a relationship with a customer of the entity or financial institution. For purposes of this invention, the term "user," "customer," and "patient" may be used interchangeably, unless indicated otherwise.

As used herein, a "user interface" may be a graphical user interface. Typically, a graphical user interface (GUI) is a type of interface that allows users to interact with electronic devices such as graphical icons and visual indicators such as secondary notation, as opposed to using only text via the command line, such as those associated with the databases. That said, the graphical user interfaces are typically configured for audio, visual and/or textual communication. In some embodiments, the graphical user interface may include both graphical elements and text elements. The graphical user interface is configured to be presented on one or more display devices associated with user devices, entity systems, processing systems and the like. The transformed/mapped/derived one or more second types of data structures having a second ICD based coding are typically presented on the user interface, e.g., based on user information and/or first type of data structure information input through the user interface.

As described above, a conventional medical diagnostic database typically comprises data structures of a particular first type and associated attributes of each the data structures. For instance, the first type of data structures may comprise International Statistical Classification of Diseases and Related Health Problems 10 (ICD-10) based coding system. On Oct. 1, 2015, care-providers within the United States transitioned to the 10th revision of the International Statistical Classification of Diseases and Related Health Problems (ICD-10) based coding system, as mandated by the Centers for Medicare & Medicaid Services (CMS). The ICD-10 coding system is a systemic rethinking of disease and procedural classification from the ninth revision (ICD-9) leading to a number of challenges with assessing populations across the ICD-9 to ICD-10 time periods.

However, in some instances, analysis of these first type of data structures having ICD-10 based coding requires transforming the first type of data structures having ICD-10 based coding to a second type of data structures comprising International Statistical Classification of Diseases and Related Health Problems 9 (ICD-9) based coding system. There is a need for maintaining consistent analysis across the ICD-10 transition period. Observed complications, comorbidities, cohort definitions, and patient risk are redefined under the ICD-10 system, each with varying levels of stability across the transition. It is therefore important to ensure that shifts in performance reflect changes in quality and not the coding system transition itself.

However, conventional medical diagnostic databases are neither configured to nor are capable of mapping/transforming the first type of data structure having ICD-10 based coding to the second type of data structure having ICD-9 based coding at all, much less transforming the data structure such that equivalence of data attributes of the data structures such as diagnosis and procedure codes are maintained after the transformation. Moreover, conventional databases are further incapable of incorporating/integrating a data attributes of a third data structure (e.g., user information) into the foregoing transformation. The advanced technical database processing and data structure transformation of the present invention ameliorates the foregoing deficiencies of conventional database technology, particularly in the medical diagnostic database context, and also provides several advantages and improvements. The technology, features, and functions of the novel comprehensive data transformation system of the present invention will be described in detail below.

FIG. 1 illustrates a comprehensive data transformation system environment 100, in accordance with one embodiment of the present invention, configured for transformation of data structures to maintain data attribute equivalency in medical diagnostic databases. As illustrated in FIG. 1, the data transformation system 106 is operatively coupled, via a network 101 to one or more database systems (108a, 108b), the user system/device 104, and to the third party system 160. In this way, the data transformation system 106 can send information to, and receive information from the one or more database systems (108a, 108b), the user system 104 and the third party system 160 to analyze and modify, in real-time, data structures and their interdependencies across a plurality of database systems (108a, 108b). FIG. 1 illustrates only one example of an embodiment of the comprehensive data transformation system environment 100, and it will be appreciated that in other embodiments one or more of the systems, devices, or servers may be combined into a single system, device, or server, or be made up of multiple systems, devices, or servers.

In some embodiments, the data associated with the data structures of the databases, may be generated by, provided by, accessed by and/or operated upon by the data transformation system 106, by the one or more database systems (108a, 108b), the user device 104 and/or other external or third party systems 160. For example, the system 106 may establish operative communication channels with the one or more database systems (108a, 108b), via the network 101. The system 106 may construct, or cause the first database system 108a to construct, a first type of data structure (e.g., source data structure) having a first ICD based coding (ICD-10), including one or more attributes comprising associated with the first type of data structure and the like, at the first database system 108a. The system 106 may construct, or cause the second database system 108b to construct, a second type of data structure (e.g., target data structure) having a second ICD based coding (ICD-9), including one or more attributes comprising associated with the second type of data structure and the like, at the second database system 108b. Continuing with the example, in some embodiments, the system 106 may further construct or cause the database system (108a, 108b) to construct, mapping/relationship(s) between the first type of data structure and the second type of data structure. In some embodiments, the data structures, the attributes and/or the associated information may be provided by users 102 using the user device 104.

As described previously, the user 102 may refer to employees, technical subject matter experts, operators and other personnel associated with the entity or affiliates of the entity.

The databases comprising the plurality of data structures are typically stored in the one or more database systems (108a, 108b). In some embodiments the records (information associated with the data structures, attributes etc.) from the activity record database may be retrieved or accessed based on satisfying requisite authentication/authorization requirements. However, it is contemplated that some or all of the records may be stored in other memory locations/devices, for example, memory device 140, the user device 104, technology resources 150 and the like.

In some embodiments, each of the database systems (108a, 108b) may comprise a database control system, which is configured to receive user-submitted queries and manage run time access to the database. The conversion of user-submitted queries may be achieved through a query processor, which may translate the queries and/or commands inputted by the user into low level instructions which may then be executed by the runtime database manager. In this way, the database systems (108a, 108b) are able to provide a layer of abstraction through which the user may use identifiable commands to execute the addition, deletion, modification, querying, and retrieval functions of the database. The database control system may further serve the function of maintaining the structure and fidelity of the data by the use of error checking and/or correction.

In some embodiments, each of the database systems (108a, 108b) may further comprise a database engine which controls, secures and provides access to the data. The database engine may be responsible for authorizing and/or authenticating users and restricting some functions of the database depending on the user class. For instance, an administrator of the entity's systems may be provided with the least restrictive rule set, which may allow the administrator to freely add, remove, edit, and query the data within the database. On the other hand, a client of the entity may be provided only with access to the query functions of the database, while a member of the public may be precluded from utilizing some or any of the functions of the database.

The database systems (108a, 108b) may further comprise a report generation utility which extracts information from the databases and presents it to the user in a number of different formats. The user 102 may be able to select specific records for viewing in a desired format, such as graphs, charts, tables, formatted text, and the like. As the system allows for increasingly complex data mapping and relationships, the report generation utility is also able to display the complex data in a way that is most relevant and comprehensible to the user.

The network 101 may be a global area network (GAN), such as the Internet, a wide area network (WAN), a local area network (LAN), near field communication network, audio/radio communication network, ultra-high frequency wireless communication network, or any other type of network or combination of networks. The network 101 may provide for wireline, wireless, or a combination wireline and wireless communication between devices on the network 101.

In some embodiments, the user 102 is an individual associated with the entity. In some embodiments, the user 102 may access the data transformation system 106 through an interface comprising a webpage or a user technology application 122. Hereinafter, "user technology application" is used to refer to an application on the user system 104 of a user, a widget, a webpage accessed through a browser, and the like. In some embodiments the user technology application 122 is a user system application stored on the user system 104. In some embodiments the user technology application may refer to a third party application or a user application stored on a cloud used to access the resource processing system through a network. In some embodiments, at least a portion of the user technology application 122 is stored on the memory device 140 of the data transformation system 106. The user 102 may subsequently navigate through the interface, retrieve one or more activity records, provide confirmation, or review presented information using a user system 104.

FIG. 1 also illustrates the user system 104. The user system 104 generally comprises a communication device 110, a display device 112, a processing device 114, and a memory device 116. The user system 104 is a computing system that allows a user 102 to interact with the data transformation system 106 to configure, analyze, transform monitor or control data structures of the databases. The processing device 114 is operatively coupled to the communication device 110, the display device 112, and the memory device 116. The processing device 114 uses the communication device 110 to communicate with the network 101 and other devices on the network 101, such as, but not limited to the third party system 160 and the data transformation system 106. As such, the communication device 110 generally comprises a modem, server, or other device for communicating with other systems/devices on the network 101. In some embodiments the network 101 comprises a network of distributed servers.

The user system 104 comprises computer-readable instructions 120 stored in the memory device 116/data storage, which in one embodiment includes the computer-readable instructions 120 of the user technology application 122. In this way, a user 102 may remotely communicate with the data transformation system 106, view retrieved data and visual displays, and/or modify the implementation of information technology operational activities using the user system 104 and the database systems (108a, 108b). The user system 104 may be, for example, a desktop personal computer, a mobile system, such as a cellular phone, smart phone, personal data assistant (PDA), laptop, or the like. Although only a single user system 104 is depicted in FIG. 1, the system environment 100 may contain numerous user systems 104.

As further illustrated in FIG. 1, the data transformation system 106 generally comprises a communication device 136, a processing device 138, and a memory device 140. As used herein, the term "processing device" generally includes circuitry used for implementing the communication and/or logic functions of the particular system. For example, a processing device may include a digital signal processor device, a microprocessor device, and various analog-to-digital converters, digital-to-analog converters, and other support circuits and/or combinations of the foregoing. Control and signal processing functions of the system are allocated between these processing devices according to their respective capabilities. The processing device may include functionality to operate one or more software programs or one or more modules, based on computer-readable instructions thereof, which may be stored in a memory device.

The processing device 138 is operatively coupled to the communication device 136 and the memory device 140. The processing device 138 uses the communication device 136 to communicate with the network 101 and other devices on the network 101, such as, but not limited to the one or more database systems (108a, 108b), the third party system 160 and the user system 104. As such, the communication device 136 generally comprises a modem, server, or other device for communicating with other devices on the network 101.

As further illustrated in FIG. 1, the data transformation system 106 comprises computer-readable instructions 142 stored in the memory device 140, which in one embodiment includes the computer-readable instructions 142 of a resource application 144 configured for systematic data processing of a plurality of information technology operational activities.

As further illustrated by FIG. 1, the system environment 100 further comprises a one or more database systems (108a, 108b). The system environment 100 may further comprise technology resources such as system hardware, technology devices and applications, operating systems, servers, technology applications, internal networks, storage/databases, user interfaces, authentication operations, middleware, program products, external networks, hosting/facilities, business/technology processes, and other technology resources or technology assets associated with the entity, not illustrated herein.

As discussed, conventional medical diagnostic databases are neither configured to, nor are capable of, mapping/transforming the first type of data structure having ICD-10 based coding to the second type of data structure having ICD-9 based coding at all, much less transforming the data structure such that equivalence of data attributes of the data structures such as diagnosis and procedure codes are maintained after the transformation. Moreover, conventional databases are further incapable of incorporating/integrating a data attributes of a third data structure (e.g., user information) into the foregoing transformation. The advanced technical database processing and data structure transformation of the present invention ameliorates the foregoing deficiencies of conventional database technology, particularly in the medical diagnostic database context, and also provides several advantages and improvements. Specifically, in some embodiments, the present system provides data structure transformation based on a novel comprehensive data transformation/mapping system (referred to as the "system") of the present invention that overcomes deficiencies of both (i) General Equivalence Mapping of data structures and (ii) Reimbursement Mapping of data structures, each of which are deficient in that they are inaccurate and error prone, resulting in increased consumption of time, processing power and memory resources. Moreover, the novel comprehensive data transformation system of the present invention provides a highly accurate transformation between data structures (e.g., ICD-10 based coding to ICD-9 based coding) while maintaining data attribute equivalence across the transformation, with reduced time, processing and memory requirements. A brief summary of the two mappings and the alternative approach are provided below.

The deficiencies of General Equivalence Mapping and Reimbursement Mapping are described in detail below. The General Equivalence Mapping (GEMs) may be employed to provide mappings between ICD-10 and ICD-9 coding systems. For each source ICD code (e.g., a first data structure having an ICD-10 based coding system), the GEMs mapping provides one or more "scenarios" to which a source code can be mapped. A scenario is defined by one or more target ICD codes (e.g., one or more second data structures having an ICD-9 based coding system), along with their relative rank. However, this type of mapping is deficient because it requires an additional decision process, within GEMs, to identify the most appropriate derived code(s) with general equivalency to the source code, making it error prone and unreliable and causes the results to fluctuate. In some instances, GEMs based mapping is flawed, in that it may simply return a "no match" result for certain first data structure having an ICD-10 based coding system even though corresponding one or more second data structure having an ICD-9 based coding system are present. Moreover, GEMs based mapping time intensive and expensive.

The Reimbursement Mapping (R-MAP) may be derived from GEMs. However, it differs in that it only provides one directional equivalency from ICD-10 based coding systems to ICD-9 based coding systems. In some instances the R-MAP may provide a single scenario. However, the R-MAP causes an undesirable loss of clinical precision, in that, many data structures having ICD-9 based coding can never be constructed/derived through the mapping (e.g., a "no match" result). The R-MAP is also incapable of incorporating/integrating a data attributes of a third data structure (e.g., user information), resulting in all users (e.g., patients) being treated as identical, even though the users are often distinct, clinically and physiologically, leading to a loss in clinical granularity across the mapping.

The unique, technology-centric, data structure transformation based on a novel comprehensive data transformation/mapping system of the present invention overcomes deficiencies of both (i) General Equivalence Mapping of data structures and (ii) Reimbursement Mapping of data structures. Amongst many improvements to technology provided, the present invention is configured for incorporating/integrating a data attributes of a third data structure (e.g., comprising data attributes associated with the unique clinical conditions and physiological parameters of each user in the form of metadata) into transformation of a first data structure to a second data structure, which would not be possible in the absence of the present invention. The present invention further provides both clinical richness and user-specific probabilistic mapping, in such a way, so that the present invention can be applied in large scale without the dual coding requirement on the part of the clinical coder, while still maintaining accurate data attribute equivalency across the transformation, which would not be possible in the absence of the present invention.

Embodiments of the unique, technology-centric, data structure transformation based on a novel comprehensive data transformation/mapping system of the present invention will be described in greater detail below, and later on through this description. In some embodiments, the comprehensive data transformation system of the present invention is configured to construct a coding/classification model that probabilistically identifies, at a user (e.g., patient) level, the most likely data structure having ICD-9 based coding, for a particular data structure having ICD-10 based coding. Here, in some embodiments, a separate coding/classification model is built for each data structure having ICD-10 based coding. In some instances, the target data structures (i.e. one or more data structures having ICD-9 based coding) may be restricted to those available in the enriched GEMs mapping.

Now referring to FIG. 2, FIG. 2 illustrates a high level schematic representation 200 of data transformation across database systems of different data structure types (i.e., different ICD based coding), in accordance with some embodiments of the invention. Specifically, FIG. 2 depicts a line and symbol diagram representation of some of the data structures that may exist within the multidimensional databases, in accordance with some embodiments of the present invention. FIG. 2 illustrates a non-limiting example of the data transformation/mapping across ICD codes.

As discussed, the comprehensive data transformation system 106 of the present invention is configured for transforming a first type of data structure to a second type of data structure while still maintaining attribute equivalency. The "first type of data structure" may also be referred to as a "source data structure" herein. As such, the first type of data structure/source data structure may comprise a first ICD based coding, such as ICD-10 based coding. Typically, a first database system 210 (e.g., similar to the first database system 108*a* or the database system 108*a* itself) may store a plurality of first type of data structures/source data structures (e.g., 1A-1D), each corresponding to an associated ICD-10 based code. The "second type of data structure(s)" may also be referred to as a "target data structure(s)" herein. As such, each of the one or more second type of data structures/target data structures may comprise a second ICD based coding, such as ICD-9 based coding. Typically, a second database system 250 (e.g., similar to the second database system 108*b* or the database system 108*b* itself) may store a plurality of second type of data structures/target data structures (e.g., 2A-2E), each corresponding to an associated ICD-9 based code.

Specifically, FIG. 2 illustrates data structures of a portion of a first database 210, in accordance with some embodiments. This database 210 may be stored at or be similar to the first database system 108*a* and is typically associated with a plurality of first type of data structures/source data structures (e.g., 1A-1D), each corresponding to an associated ICD-10 based code. FIG. 2 further illustrates data structures of a portion of a second database 250, in accordance with some embodiments. This database 250 may be stored at or be similar to the second database system 250 and is typically associated with a plurality of second type of data structures/target data structures (e.g., 2A-2E), each corresponding to an associated ICD-9 based code.

The comprehensive data transformation system 106 of the present invention is configured for transforming/mapping a first type of data structure to a second type of data structure. Specifically, FIG. 2 illustrates a first transformation "T1" of the source data structure 1A of ICD-10 based code to target data structure 2A of ICD-9 based code. Similarly, FIG. 2 also illustrates a second transformation "T2" of the source data structure 1B of ICD-10 based code to two target data structures 2B and 2C of ICD-9 based code. FIG. 2 also illustrates a third transformation "T3" of the source data structure 1D of ICD-10 based code to two target data structures 2D and 2E of ICD-9 based code. Although not illustrated, the transformation may comprise a two or more source data structures being transformed/mapped to one target data structure, and/or overlap of source/target data structures across various transformations.

Moreover, as discussed, the comprehensive data transformation system of the present invention is configured for incorporating/integrating a data attributes of a third data structure (e.g., comprising data attributes associated with the unique clinical conditions and physiological parameters of each user). This "third data structure" or "third type of data structure" may also be refer to as a "feature data structure" herein. Here, in some embodiments, the present invention integrates user-level/patient-level characteristics as the basis for transformation/mapping steps/decisions within the available mapping reference data. The third data structure/feature data structure may comprise user data. This user data may comprise one or more of the user/patient's clinical conditions (e.g., diagnostic history) and physiological parameters (e.g., demographic information). In some embodiments, the invention integrated only a portion of the user data that is determined to have a predetermined/meaningful impact on transformation accuracy. It is noted that "user" and "patient" may be interchangeably used in some embodiments. FIG. 2 illustrates, a third/user data structure 3A comprising user information of a first user being integrated with or forming a basis for transformation T1. FIG. 2 further illustrates, another third/user data structure 3B comprising user information of a second user being integrated with or forming a basis for transformation T3.

As such, the user data of third data structure/feature data structure may comprise patient/user attributes such as a Patient Type data (e.g., a predetermined patient type, value and/or category), Gender data (e.g., M, F, or U), Age Group data (e.g., discretized into 5 bins, 10 bins, etc.), Discharge Status data (e.g., a predetermined Uniform Billing (UB-04) value), Point of Origin data (e.g., a predetermined UB-04 value), Admit Type data (e.g., a predetermined UB-04 value) and/or Medicare Severity Diagnosis Related Groups (MS-DRG) data (e.g., a predetermined grouping based on ICD-10 codes). In some embodiments, at least a portion of or all of the user data may be in the form of metadata.

In some embodiments, the comprehensive data transformation system of the present invention employs reference data. In an effort to develop a more complete set of target data structures (i.e. one or more data structures having ICD-9 based coding) for a given source data structure (i.e., data structure having ICD-10 based coding), the present invention integrates supplemental metadata to handle third data structures (e.g., derived neonatal birthweight codes).

FIG. 3 illustrates a high level process flow 300 for transformation of data structures to maintain data attribute equivalency in medical diagnostic databases, in accordance with some embodiments of the present invention. One or more steps of the high level process flow 300 may be performed by the data transformation system 106, and/or the data transformation system may transmit control instructions to and cause the databases (108a, 108b), the user device 104, and/or the third party system 160 to perform one or more steps herein. As discussed, the comprehensive data transformation system 106 of the present invention is configured for transforming a first type of data structure to a second type of data structure while still maintaining attribute equivalency. As discussed, the system 106 (referred to as "the system" herein) is in operative communication with a first database (108a, 210) and a second database (108b, 250), as described with respect to FIGS. 1 and 2. The first database typically comprises a plurality of source data structures associated with a first coding type, such as ICD-10 based coding. The second database typically comprises a plurality of target data structures associated with a second coding type, such as ICD-9 based coding. The at least one processor 138 of the system 106 is operatively coupled to the least one memory device 140 and the network communication device 136. The at least one processor 138 is configured to execute the computer-readable program code to perform one or more steps of the process flow 300 described below.

As illustrated by block 302, the system is structured to receive a feature data structure comprising user information associated with a first user. The user information may further comprise user identifying information such as demographic information (e.g., gender data (e.g., M, F, or U), age group data (e.g., discretized into 5 bins, 10 bins, etc.). Next at block 304, the system is configured to retrieve user visit information. The user visit information typically comprises one or more patient attributes such as a patient type (e.g., a predetermined patient type, value and/or category), a patient class (e.g., a predetermined class/category), a point of origin (e.g., a predetermined UB-04 value), an admit type (e.g., a predetermined UB-04 value), a discharge status (e.g., a predetermined Uniform Billing (UB-04) value), and/or Medicare Severity Diagnosis Related Groups (MS-DRG) data (e.g., a predetermined grouping based on ICD-10 codes). In some embodiments, at least a portion of or all of the user data may be in the form of metadata.

As alluded to previously, care-providers within the United States transitioned to the 10th revision of the International Statistical Classification of Diseases and Related Health Problems (ICD-10) based coding system on Oct. 1, 2015, as mandated by the Centers for Medicare & Medicaid Services (CMS). Accordingly, in some embodiments, prior to proceeding to step 306, the system may first determine whether a discharge patient attribute, i.e., discharge status (e.g., a predetermined Uniform Billing (UB-04) value) associated with a second user succeeds a predetermined time interval. This predetermined time interval may be Oct. 1, 2015, a transition time period, or another date or time interval. The system may proceed with the rest of the steps, i.e., transform the first source data structure to the first target data structure when the discharge patient attribute associated with the first user succeeds a predetermined time interval, e.g., because after the time interval, only ICD-10 based codes would be available. On the contrary, the discharge patient attribute associated with the first user precedes a predetermined time interval, the system may simply retrieve the available associated target data structure (e.g., ICD-9 based code).

Next, at block 306 the system is configured to determine a source data structure (e.g., ICD-10 based coding) based on at least the received user information. As discussed, the first source data structure comprises the first coding type, e.g., ICD-10 based coding. Here, the system may determine one or more source attributes associated with the first source data structure. The first source data structure is typically associated with a first ICD code (e.g., a specific code identifier) of the first coding type. Moreover, the one or more source attributes comprise an ICD type (e.g., diagnosis or procedure), an ICD class (e.g., principal, secondary, admitting etc.), a rank (e.g., based on a predetermined ranking) and/or a present on admission (POA) indicator. The user information may be associated with one or multiple source data structures. As such, the system is configured to determine all pertinent source data structures.

As illustrated by block 308, for each source data structure, the system is configured to perform steps 310, 312 and/or 314 (e.g., iteratively, or sequentially). As illustrated by block 310, the system is first configured to assign a feature weight category. Here, the system may determine a probable set, i.e., one or more probable target data structures of the plurality of available target data structures of the second type (e.g., ICD-9 based codes) that the source data structure is required to be transformed/mapped into, e.g., based on at least the visit information and the user information. The system may determine one or more probable target data based on determining an inpatient principle diagnosis code. The system may determine one or more probable target data based on determining an inpatient other ICD code distinct from the inpatient principal diagnosis code. The system may determine one or more probable target data based on determining an outpatient principal diagnosis code. The system may determine one or more probable target data based on determining an outpatient other diagnosis code distinct from the outpatient principal diagnosis code. The system may perform some or all of the foregoing steps to construct a probable set, i.e., one or more probable target data structures that the source data structure may be mapped to.

Next at block 312, the system may determine a most probable scenario out of the probable set, i.e., one or more probable target data structures that is most accurate. Here, the system may determine, for each of the one or more probable target data structures, a probability of class for the first source data structure. The determination of the probability of class is typically based on Naïve Bayes, and is described in detail later on. The system may then map the first source data structure to the first target data structure of the one or more probable target data structures based on determining that the first target data structure comprises a highest probability of class. In other words, the first target data structure having the highest probability of class out of all of the probable data structures in the set, represents the most correct/accurate transformation. Moreover, this first target data structure is associated with a first ICD code of the second coding type, e.g., particular ICD-9 code.

Next at block 314, the system is further configured to determine one or more attributes associated with the source data structure and/or probable target data structures. As discussed previously, wherein one or more target/source attributes comprise an ICD type, an ICD class, a rank and/or a Present on Admission (POA) indicator. In this way, the system transforms the first source data structure to the first target data structure such that (i) the first target data structure comprises the second coding type, e.g., the ICD-9 based coding, and (ii) one or more target attributes associated with the first target data structure are equivalent to the one or more source attributes associated with the first source data structure. Subsequently, the system is configured to determine a target data structure associated with the one or more attributes, as illustrated by block 316. The system may then initiate a presentation of the first target data structure on a display device associated with a user device at block 318, via a user interface of the user device. The system is configured to further update a historical mapping database (not illustrated) with the first source data structure and the first target data structure, thereby implementing a self-learning feature.

The determination of the probability of class and the transformation/mapping process of data structures of the present invention in general will now be described. Here, the invention may identify the most likely target transformation/mapping scenario (e.g., one or more target data structures having ICD-9 based coding, such as within/in addition to GEMs) for a given user/patient's source data structure having ICD-10 based coding, based on a unique Naïve Bayes implementation. The present invention may construct Naïve Bayes to identify the likelihood that a given source data structure belongs to a class of target data structures based on previous classifications of source data structures to their respective target data structures. This likelihood may be constructed as the class probability given the source data structure or P(c|d). As such, P(c|d) is constructed to indicate the likelihood of a particular target data structure having ICD-9 based coding, or set of one or more target data structures having ICD-9 based coding "c", given a unique user's source data structure having ICD-10 based coding "d". In some instances, "d" may be referred to as document(s). In other words, a given user/patient's source data structure having ICD-10 based coding may be referred to as "documents" or "d," while the mapping scenario, i.e., one or more target data structures having ICD-9 based coding may be referred to as "classes" or "c". Accordingly, P(c|d) may be constructed based on the following correlation:

$$P(c|d) = \frac{P(c)P(d|c)}{P(d)}$$

Here, "P(c)" may refer to the probability of the class within the corpus, "P(d)" may refer to the probability of the document within the corpus, and "P(d|c)" may refer to the probability of the document within the class. The system is configured to construct P(c|d) for each scenario for a source data structure having ICD-10 based coding, within the highest confidence class "$C_{MAP}$" being the assigned-scenario for that source data structure having ICD-10 based coding, as described below.

In some embodiments, the system may construct and evaluate each scenario for a source data structure having ICD-10 based coding, with a highest confidence class "$C_{MAP}$" being the assigned-scenario for that coded source data structure. $C_{MAP}$ may be constructed as arguments of the maxima:

$$C_{MAP} = \mathrm{argmax}(P(c|d)), \text{ i.e., } C_{MAP} = \mathrm{argmax}\frac{P(c)P(d|c)}{P(d)}$$

Here, "$C_{MAP}$" may refer to The highest probability candidate class for a given document (maximum a posteriori), while argmax may indicate that the maximum value from the equation right of the equals sign should be used as the highest probability candidate.

Next, the system may construct the Class Probability "P(c)" indicated above. The probability of a class (or scenario) simply indicates how representative a class is of the larger corpus. Class probability may be defined by the distinct count of users/patients within an target data structures having ICD-9 based coding transformation scenario for a given source data structure having ICD-10 based coding "$|X_{wy}|$" over the superset of users/patients (e.g., within the training set) "$|X_y|$", with each user/patient "x" being a member of the larger set "X" or {x∈X}, as indicated below. In some instances, here, the class probability, identifies the general likelihood of the transformation scenario itself. Moreover, in some embodiments, high-volume scenarios may be weighted higher than low-volume scenarios.

$$P(c) = \frac{|X_{wy}|}{|X_y|}$$

Here, "y" refers to the scope of data within a given source data structure having ICD-10 based coding, while "w" refers to the scope of data within a set of one or more target data structures having ICD-9 based coding (e.g., GEMs) scenario.

Next, the system may construct the Document Probability "P(d|c)" indicated above. The document probability given the class, or P(d|c), determines the likelihood of a user/patient's respective clinical attributes and/or physiological information occurring within the scope of one or more target data structures (e.g., a GEMs scenario). For each ICD-9 scenario, "w", the probability of each user/patient's attribute, "z", is determined:

$$p_{wyz} = \frac{|X_{wyz}|}{|X_{wy}|}$$

Moreover, the system may further transform the above, by implementing Laplace smoothing to account for instances where the probability of a user/patient's attribute within a given scenario is zero. Thereby, the system prevents the cascading effect throughout the larger Naïve Bayes construction steps that results in a total probability of zero for that scenario:

$$p_{wyz} = \frac{|X_{wyz}| + s}{|X_{wy}| + |X_{wy}|s}$$

Finally, to achieve the Document Probability "P(d|c)" given the class (or the probability of a user/patient's unique attributes given a GEMs scenario), the product of the weighted-attribute probabilities is calculated as follows:

$$P(d \mid c) = \prod p_{wyz_i}{}^{w_{z_i}}$$

Next, with respect to the Document Probability "P(d)" indicated above, given that (i) P(d) is a constant within the one or more target data structures scenarios (e.g., a GEMs scenarios) associated with an a given source data structure having ICD-10 based coding, and (ii) that scenario classification is always driven through the maximum probability (therefore eliminating the need for a normalized confidence threshold at which a classification decision is made), P(d) may not evaluated within the model, as is common with maximum a posteriori classifiers in some instances.

An entity/facility's structural composition may naturally vary (given its patient mix, physician specialties, bed types, coding practices, etc.). Accordingly, in some embodiments, the system may perform facility stratification configured to better account for the unique distribution of historical ICD-9 codes, potentially driven by the unique nature of that facility. This construction/transformation based on facility specific data associated with the facility of a user/patient results in an adaptive and tailored to each individual user/patient and the associated entity/facility, which additionally increases the accuracy of the transformed target data structures having ICD-9 based coding. The steps performed for stratification are described below. First, probabilities based on historical user data may be employed by the system (i.e. via Naïve Bayes) in order to select the most appropriate GEM scenario for a given ICD-10, or source code. When estimating probabilities using the facility-stratified model, the information known about the greater sub-set of patients (i.e. all available user data) may be imposed as a bias on the facility-level probabilities, by the system. This "smoothing" avoids over-fitting a single facility—especially if that facility has a low patient volume, thereby providing an additional improvement over conventional systems.

Here, the system may perform a Bernoulli distribution when using a sample to estimate the probability of a binary output, such as a class/scenario. This function represents the probability density function, or PDF, of a binary decision, where a condition is either true or not. In this instance, the system determine the probability of a GEM scenario for a particular facility.

$X$={all available user/patient data}

$f(p) = p^{|X_{hsy}|}(1-p)^{(|X_{hy}|-|X_{hsy}|)}, p \in (0,1)$

Here, h may refer to the scope of data within a given facility, y may refer to the scope of data within a given source code, and s may refer to the scope of data within a given GEM scenario.

In the embodiments where facility stratification is performed, the class probability bay be constructed based on:

$$P(c) = \frac{|X_{wy}| + \alpha + s}{(|X_y| + \alpha + \beta) + |X_y|s}$$

$$p_{wyz} = \frac{|X_{wyz}| + \alpha + s}{(|X_{wy}| + \alpha + \beta) + |X_{wy}|s}$$

Here, $\alpha$ and $\beta$ may be determined based on constructing a Beta distribution of the Bernoulli distribution, while s may be determined based on performing Laplace smoothing.

Moreover, in some embodiments, the system is structured to assign weights to the features/scenarios, as alluded to above. Naïve Bayes comprises a drawback because it treats raw features (user data attributes) comprising P(d|c) equally, even though clinical and physiological attributes of the user data have varying impact to transformation/mapping accuracy and performance. In order to resolve this problem, the present invention provides a Gradient Descent approach which is structured to better handle (i) potential conditional dependence, (ii) magnitudinal differences, and (ii) natural variability observed within those feature/user data attribute probabilities.

In some embodiments, separate feature weight vectors (or vector components) are employed to better discriminate the relative impact that each feature (user data attribute) has within a defined set of subgroups. In order for the system to support a wide variety of patients, feature-weight (user data attribute-weight) values are stratified by sub-populations. As such, features/user data attributes deemed significant for one subset of users/patients may not be the same for another (e.g. MS-DRG is not relevant for patients seen in the outpatient setting). Accordingly, features/user data attributes with negligible impact on model performance may be excluded in some embodiments.

Moreover, in some embodiments, the system further implements a Gradient Descent of the feature weight vectors, e.g., via a batch learning rate process, Here, the weights may be modified once per epoch using an average of the error weights across all scenarios. The system calculates mean errors for every feature within the scope of each sub-population in order to calculate the delta impact on the feature weight. The result is then multiplied by the learning rate to get this delta value. Finally, the delta value is added to the existing weight to get the updated weight. Iterations continue, with each iteration using the modified weights from the previous iteration. Through this approach, the system may continue to modify the weights until they reach a point where further iteration no longer meaningfully improves the error terms. By solving for these values through an iterative approach, any issues of non-linearity between multiple features is handled naturally as error is re-assessed after each modification. Another benefit with a Gradient Descent approach is that the feature probabilities are modeled around the static probability of the class. By modifying weights in this fashion, the impact of class probability on classification for a source code inversely correlates with the cumulative weighting of the features. As feature weights rise, the impact of the class decreases, while a decrease in feature weights result in an increase in class probability impact.

In addition, in some embodiments, in order to measure the model's ability to correctly derive/construct equivalent target data structures having ICD-9 based coding, coding alignment may be tested through Jaccard Similarity Coefficient. This may be a similarity metric defined as an intersection of the submitted target data structures having ICD-9 based coding (set A) and derived target data structures having ICD-9 based coding (set B) over the union of both submitted and derived target data structures having ICD-9 based coding. For instance, for a given user/patient ("$S_{AB}$"), a scenario where all derived target data structures having ICD-9 based coding align with all submitted target data structures having ICD-9 based coding, yields a match score of 1 (or 100%). In the event that none of the derived target data structures having ICD-9 based coding exists on the dual coded user/patient, the coefficient would be zero.

$$S_{AB} = \frac{A \cap B}{A \cup B}$$

A non-limiting example of the above construction will be described below. The example comprises a mock patient discharged from facility A, coded under the ICD-10 system. Some of the ICD-10 codes on the patient's record directly map to an ICD-9 code and therefore no decision point is required. Other ICD-10 codes within the patient record have multiple options within GEMs. However, only one of those options exists within the facility's history and therefore a direct mapping can be made. The ICD-10 code "R65.21" is an example of this scenario, as it has 2 potential maps within GEMs (ICD-9 code 785.52 or ICD-9 codes 785.52 and 995.92). Given that one of these scenarios (the joint occurrence of 785.52 and 995.92) never occurs in the facility's historical data, the ICD-10 code R65.21 is mapped directly to ICD-9 code 785.52, as indicated by Table 1 below.

TABLE 1

Patient ICD-10 Coding

| ICD-10 | Type | POS | 1:1 Map | ICD-9 |
|---|---|---|---|---|
| A41.9 | D | 1 | 0 | ? |
| R65.21 | D | 2 | 1 | 785.52 |
| J96.20 | D | 3 | 0 | ? |
| J15.212 | D | 4 | 1 | 482.42 |
| N17.9 | D | 5 | 1 | 584.9 |
| E86.0 | D | 6 | 1 | 276.51 |
| E03.9 | D | 7 | 1 | 244.9 |
| I10 | D | 8 | 0 | ? |

Next, each remaining ICD-10 code is evaluated using the probabilistic approach outlined in the larger document. The ICD-10 code "I10" is evaluated, and further determination is made regarding which of the possible GEMs scenarios is the most likely candidate for this patient. This ICD-10 code has three possible ICD-9 code scenarios that it could be mapped to according to GEMs: 401.0, 401.1, or 401.9. Each of these scenarios are referred to as "classes", and each of these classes have a probability of being coded based on the frequency of these codes within facility A's coding history. The likelihood of the scenarios is indicated in Table 2 below. It is noted that scenario 3 has the highest class probability with 91%.

TABLE 2

Evaluating ICD-10 Code of I10

| Scenario 1 | | Scenario 2 | | Scenario 3 | |
|---|---|---|---|---|---|
| ICD-9 Code | Probability of the Class | ICD-9 Code | Probability of the Class | ICD-9 Code | Probability of the Class |
| 401.0 | 0.64% | 401.1 | 8.63% | 401.9 | 91.00% |

The above result is comparable to the Reimbursement Mapping approach in that scenario probabilities alone drive the coding decision. The statistical model builds upon scenario probabilities by further considering the patient's unique demographic and clinical conditions to estimate the most likely scenario. Up to nine (or more) patient specific features are considered when evaluating the patient level probability of each class: Admit Type, Age, Discharge Status, Gender, Patient Class, MS-DRG, Patient Type, and Point of Origin, as alluded to previously.

The above-stated features are used to calculate the probability of the document. The document in this case is the ICD-10 code on this particular patient, which is described through its features. Each of these attributes have a given probability within each scenario. As an example, an Admit Type of Emergency exists on 92.64% of the patients that are coded with scenario 1 based on facility A's historical data. The attributes listed at Table 3 are for the patient being evaluated. Because this ICD-10 code is a secondary diagnosis code for an inpatient, the respective feature (or patient attribute) weights for that code type have also been included in the Table 3. These feature weights are then multiplied by the probability of each attribute to yield the Weight-Adjusted Probabilities. Once these have been calculated for each attribute within a scenario, their collective product will yield the "probability of the document". A document probability is determined for each scenario.

TABLE 3

Patient Attributes
Probability of the Document
(Product of Smoothed Probabilities)

| | | Scenario 1 0.00021% | | Scenario 2 0.00045% | | Scenario 3 0.00001% | |
|---|---|---|---|---|---|---|---|
| Attribute | Feature Weights | Smoothed Probability | Weight Adj. Probability | Smoothed Probability | Weight Adj. Probability | Smoothed Probability | Weight Adj. Probability |
| Admit Type of Emergency | 1.3962422 | 92.64% | 129.34% | 76.61% | 106.97% | 84.84% | 118.45% |

TABLE 3-continued

| | | Patient Attributes Probability of the Document (Product of Smoothed Probabilities) | | | | | |
|---|---|---|---|---|---|---|---|
| | | Scenario 1 0.00021% | | Scenario 2 0.00045% | | Scenario 3 0.00001% | |
| Attribute | Feature Weights | Smoothed Probability | Weight Adj. Probability | Smoothed Probability | Weight Adj. Probability | Smoothed Probability | Weight Adj. Probability |
| Age within 60-79 years | 1.0134987 | 42.64% | 43.22% | 49.13% | 49.80% | 39.63% | 40.17% |
| Discharge Status of Discharged/Transferred to SNF | 0.5838308 | 6.76% | 3.95% | 10.97% | 6.40% | 3.68% | 2.15% |
| Gender of Male | 0.2139005 | 41.17% | 8.81% | 42.75% | 9.14% | 44.33% | 9.48% |
| Patient Class of Inpatient | n/a | 78.82% | | 71.35% | | 26.00% | |
| MS-DRG of 871 | 0.1824577 | 2.06% | 0.38% | 3.17% | 0.58% | 1.15% | 0.21% |
| Patient Type of Inpatient | 2.170334 | 78.82% | 171.06% | 71.35% | 154.85% | 26.00% | 56.43% |
| Non-healthcare Facility Point of Origin | 1.0579505 | 97.05% | 102.67% | 94.33% | 99.80% | 97.41% | 103.06% |

The product of the document and class probabilities will produce the final non-normalized probability, allowing the most likely scenario to be identified as having the highest probability. For this patient, 110 will map to scenario 2, or ICD-9 code 401.1.

Additionally, technical improvements provided by the comprehensive data transformation system of the present invention, which overcomes deficiencies of both (i) General Equivalence Mapping of data structures and (ii) Reimbursement Mapping of data structures, will be discussed below with respect to FIGS. 4A-4D. FIG. 4A illustrates, a user Jaccard Coefficient Performance improvement provided by the comprehensive data transformation system of the present invention, in comparison with the Reimbursement Mapping of data structures, in accordance with some embodiments of the invention. FIG. 4B illustrates, Pre-existing Diabetes in Pregnancy within the comprehensive data transformation system of the present invention and Reimbursement Mapping, in accordance with some embodiments of the invention. FIG. 4C illustrates, Salmonella Sepsis within the comprehensive data transformation system of the present invention and Reimbursement Mapping, in accordance with some embodiments of the invention. FIG. 4D illustrates, Post-Operative Wound Dehiscence Coding, in accordance with some embodiments of the invention.

Now referring to FIG. 4A, in one instance, mean facility coefficients for both R-MAP and the comprehensive data transformation system of the present invention were compared in order to evaluate each system's ability to correctly derive target data structures having ICD-9 based coding. It was found that derived codes using the comprehensive data transformation system of the present invention showed greater alignment with direct target data structures having ICD-9 based coding than those derived by R-MAP, as can be observed in FIG. 4A. This analysis was performed against an all-payer dual-coded claims database with national representation of both inpatient and outpatient users, of all ages and disease groups, across 141 acute care facilities. Facilities were required to have a minimum of 100 dual-coded patients to be included in the analysis. Reimbursement mapping resulted in a mean facility-level Jaccard coefficient of 0.665 while the comprehensive data transformation system of the present invention produced a mean value of 0.721 (z=5.05, n=141). The comprehensive data transformation system of the present invention is able to provide improved patient-level coding not achievable through a single-choice mapping system.

Given the required coding specificity, in some instances, complications have shown to be sensitive to backwards mapping, as made evident in the examples provided below. There are many scenarios within the GEMs system that a source data structure having ICD-10 based coding maps back to multiple options with only one indicating a complication. In these instances, Reimbursement Mapping is either assigning a complication to every user/patient through a direct mapping from that ICD-10 code or is never assigning a complication to patients with this code. The system of the present invention, on the other hand, will make a tailored decision based on the unique user/patient features.

As the outcomes from these two systems vary, it is important to determine which backwards mapping method derives observed complications comparable to those coded in target data structures, i.e., ICD-9 manually. Complication rates based on historically-submitted target data structures having ICD-9 based coding therefore provide a baseline against which the derived rates can be compared. Through this approach the system of the present invention more-closely aligns with the historical rates, thereby demonstrating its efficacy and accuracy. In some instances, the clinical grouping with the greatest coding variance is found to be Infectious and Parasitic Diseases. This grouping represents a population where the coding system itself has undergone many changes and no direct mapping for these source data structure having ICD-10 based coding is sufficient. This clinical group is highly impactful to observed complication measures and an improvement of accuracy within this sub-population correlates with significantly-improved alignment with historically observed complication frequencies.

Delivery vs. Antepartum Condition

Now referring to FIG. 4B, in some instances, one significant change from ICD-9 to ICD-10 based coding is the representation of pregnancy complications. An added level of specificity is included within the ICD-10 system through the qualification of the patient's trimester. However, some specificity was also lost within the ICD-10 code itself. Previously, the ICD-9 code that indicated a complication during a pregnancy also indicated whether a baby was "delivered" or the complication was an "antepartum" condition. Through the ICD-10 language, this information is no longer captured on the complication code, but inferred from the accompanying diagnosis codes/attributes.

An example using ICD-10 O24.011, "Pre-existing diabetes mellitus, type 1, in pregnancy, first trimester", will prove helpful. This source data structure having ICD-10 based coding can map back to one of two target data structures having ICD-9 based coding within the GEMs mapping: (i) 648.01: "Diabetes mellitus of mother, complicating pregnancy, childbirth, or the puerperium, delivered, with or without mention of antepartum condition" or (ii) 648.03: "Diabetes mellitus of mother, complicating pregnancy, childbirth, or the puerperium, antepartum condition or complication."

As both of the above target data structures having ICD-9 based coding options are valid given the source data structure having ICD-10 based coding, additional third data structure attribute information, i.e., user/patient-level information must be observed in order to make a more informed derivation. In this circumstance, the Reimbursement Mapping derives ICD-9 code 648.01, indicating that a delivery occurred in every instance of this ICD-10. This pattern is observed with a number of related codes indicating a complication during pregnancy, with delivery always being derived through the Reimbursement Mapping method, regardless of their potential to be an antepartum condition.

In contrast, the system of the present invention makes a patient-level decision, indicating a delivery in instances where it is highly probable, and an antepartum condition in others where a delivery is less likely. FIG. 4B depicts the results of the comprehensive data transformation system of the present invention when observed for all ICD-10 codes indicating a pre-existing condition of diabetes during pregnancy. It derives very few instances of delivery during the early trimesters of pregnancy and increases the derivation of delivery codes as full term is approached. As illustrated, the two systems differ significantly for complication codes during the early trimesters of pregnancy as Reimbursement Mapping never derives an ICD-9 antepartum condition code.

Cerebrovascular Complications in Pregnancy

In some instances, obstetrics patients with complications and conditions of the circulatory system in pregnancy are another clinical population that reflect the fundamental differences resulting in improved performance by the present invention. Source data structures having ICD-10 based coding indicating the presence of a disease of the circulatory system, can map back to a number of scenarios of target data structures having ICD-9 based coding, including two different cardiovascular disorders and a cerebrovascular disorder.

For most ICD-10 codes in this family, Reimbursement mapping derives an ICD-9 code indicating a cerebrovascular disorder in puerperium. This disorder is considered a complication (e.g., a predetermined complication), whereas the cardiovascular options are not. As a result of the direct mapping, the rate of cerebrovascular complications is significantly overstated when derived through the Reimbursement Mapping. In contrast, the comprehensive data transformation system of the present invention derives the cerebrovascular complication in way that aligns with its historical likelihood, with an increased derivation of the more probable cardiovascular conditions.

Septicemia and SIRS

Now referring to FIG. 4C, in some instances, another area of high variance exists within septicemia and SIRS coding. A common pattern is observed within the family of codes that indicate the presence of an underlying condition. An example of this scenario can be observed with A02.1, Salmonella sepsis. Within the GEMs mapping, this code can result in two different options: (i) salmonella septicemia or (ii) salmonella septicemia accompanied by SIRS, a condition typically considered to be a complication.

In this instance, the derivation of the first option, including SIRS, will result in an observed complication, while the derivation of the second option, excluding SIRS, will not. In all circumstances where a specified underlying condition is indicated within ICD-10, the Reimbursement Mapping derives the first option, resulting in a complication being attributed to that patient. The comprehensive data transformation system of the present invention derives the accompanying 995.91 code on a case-by-case leading to a distribution of those codes better aligning with historical coding performance.

The source data structure having ICD-10 based coding indicating that an "unspecified" underlying condition occurred exhibits the inverse behavior to those where the presence of an underlying condition is specified. In these instances, Reimbursement Mapping always derives the underlying condition without SIRS. The present system of the invention, however, behaves as it did with the specified underlying conditions, continuing to make a user/patient-level decision.

In some instances, because complications are often reported in aggregate, the frequency of the unspecified code compared to its specified counterparts is meaningful within the overall aggregate rate. Based on the data analyzed, the unspecified code is more than 2 times as likely to be coded on a user/patient's record. The overall rate of this complication when viewing a large user/patient population is very similar between the systems, with Reimbursement mapping deriving the complication at a slightly lower rate than both the system of the present invention and historically coded data. However, as smaller groupings of patients are analyzed, the difference in these methods becomes more pronounced.

Patient Safety Indicator-14: Post-Operative Wound Dehiscence

Now referring to FIG. 4D, in some instances, Agency for Healthcare Research and Quality (AHRQ) supports a Patient Safety Indicator (PSI) measure methodology used within Centers for Medicare & Medicaid Services (CMS) reimbursement programs. Within these measures, the definition of the numerator cases for Post-Operative Wound Dehiscence (PSI-14) is highly sensitive to the transition from ICD-9 to ICD-10.

While the occurrence of this complication is defined by a single ICD-9 code (54.61) under the PSI version 6.0 (the last supported ICD-9 version of PSI), it is not represented within R-MAP and therefore cannot be derived through an ICD-10 code using this system/mapping. AHRQ makes the recommendation that ICD-10 OWQFXZZ code is equivalent and should be used to define the numerator cases in PSI version 7.0 (the first supported ICD-10 version of PSI).

Within GEMs, this particular ICD-9 code does appear as a mapping candidate for the recommended ICD-10, as can be seen in FIG. 4D. However, this class is historically observed only 6.9% of the time. A direct mapping to this code, based on the available set of dual coded data, would result in more than a three-fold increase of the rate of this complication. This would not only change the definition of the numerator, but also misalign this value with the PSI risk-adjustment, which is largely stable over the transition.

In contrast, if R-MAP is used as defined no patients after the transition to ICD-10 would be included in the numerator population. The comprehensive data transformation system of the present invention provides an approach that enables stability in the rate of this complication across the transition, deriving the impactful ICD-9 code in accordance with the historical likelihood of the code.

This stability in backwards mapping enables the continued use of PSI version 6.0 post-transition to ICD-10. This is important as AHRQ has yet to release a risk adjustment methodology for PSI version 7.0 and no ICD-10 based risk-adjustment is currently available.

The system, method and computer program product developed and discussed herein has been shown to be a reliable method of transforming and mapping data to create equivalency in longitudinal performance. Based on the findings, the comprehensive data transformation system of the present invention can be used as a way to look at historic data to help inform current performance and trends in healthcare to improve overall patient care.

Analytic techniques are developing at a rapid pace and with the increasing presence of big data in healthcare there is an ever-increasing presence of data science in healthcare that relies on historic data to train models to predict outcomes and pathways of care. If the data used in the modeling is limited, the models will not be able to sufficiently predict or anticipate the outcomes of interest. The comprehensive data transformation system of the present invention described herein allows users of coded data to take advantage of many years' experience to train models to better predict outcomes of care.

As demonstrated the comprehensive data transformation system of the present invention can be used for more specific use cases. For example, many health systems are beginning to use an ICD-10 based definition of observed complications, especially now that sufficient ICD-10 volume exists to produce coefficients used within risk-adjusted models. The underlying ICD-coding is not always equivalent across the transition period which can introduce unintended fluctuations in performance through the coding system alone.

In addition to health system concerns, researchers are reliant upon administrative and coded data to evaluate real world performance of treatments or other interventions over time. If those researches and experts do not have an adequate method to tie together ICD-9 and ICD-10 data, they will likely have inaccurate results that do not reflect the true patterns in patient diagnoses and procedures in the US healthcare system. The more accurate the mapping the more likely users of ICD data will be able to adequately evaluate changes over time, and as real world data becomes more important for multiple purposes the data must remain consistent to have meaningful real world evidence.

As demonstrated in the findings outlined herein, inaccuracies in administrative data can lead to an inadequate capture of serious conditions that are routinely monitored as part of quality performance and that are crucial for providing accurate and timely diagnoses and treatments.

Each communication interface described herein generally includes hardware, and, in some instances, software, that enables the computer system, to transport, send, receive, and/or otherwise communicate information to and/or from the communication interface of one or more other systems on the network. For example, the communication interface of the user input system may include a wireless transceiver, modem, server, electrical connection, and/or other electronic device that operatively connects the user input system to another system. The wireless transceiver may include a radio circuit to enable wireless transmission and reception of information.

As will be appreciated by one of ordinary skill in the art, the present invention may be embodied as an apparatus (including, for example, a system, a machine, a device, a computer program product, and/or the like), as a method (including, for example, a business process, a computer-implemented process, and/or the like), or as any combination of the foregoing. Accordingly, embodiments of the present invention may take the form of an entirely software embodiment (including firmware, resident software, microcode, and the like), an entirely hardware embodiment, or an embodiment combining software and hardware aspects that may generally be referred to herein as a "system." Furthermore, embodiments of the present invention may take the form of a computer program product that includes a computer-readable storage medium having computer-executable program code portions stored therein.

As the phrase is used herein, a processor may be "configured to" perform a certain function in a variety of ways, including, for example, by having one or more general-purpose circuits perform the function by executing particular computer-executable program code embodied in computer-readable medium, and/or by having one or more application-specific circuits perform the function.

It will be understood that any suitable computer-readable medium may be utilized. The computer-readable medium may include, but is not limited to, a non-transitory computer-readable medium, such as a tangible electronic, magnetic, optical, infrared, electromagnetic, and/or semiconductor system, apparatus, and/or device. For example, in some embodiments, the non-transitory computer-readable medium includes a tangible medium such as a portable computer diskette, a hard disk, a random access memory (RAM), a read-only memory (ROM), an erasable programmable read-only memory (EPROM or Flash memory), a compact disc read-only memory (CD-ROM), and/or some other tangible optical and/or magnetic storage device. In other embodiments of the present invention, however, the computer-readable medium may be transitory, such as a propagation signal including computer-executable program code portions embodied therein.

It will also be understood that one or more computer-executable program code portions for carrying out the specialized operations of the present invention may be required on the specialized computer include object-oriented, scripted, and/or unscripted programming languages, such as, for example, Java, Perl, Smalltalk, C++, SAS, SQL, Python, Objective C, and/or the like. In some embodiments, the one or more computer-executable program code portions for carrying out operations of embodiments of the present invention are written in conventional procedural programming languages, such as the "C" programming languages and/or similar programming languages. The computer program code may alternatively or additionally be written in one or more multi-paradigm programming languages, such as, for example, F#.

Embodiments of the present invention are described above with reference to flowcharts and/or block diagrams. It will be understood that steps of the processes described herein may be performed in orders different than those illustrated in the flowcharts. In other words, the processes represented by the blocks of a flowchart may, in some embodiments, be in performed in an order other that the order illustrated, may be combined or divided, or may be performed simultaneously. It will also be understood that the blocks of the block diagrams illustrated, in some embodiments, merely conceptual delineations between systems and one or more of the systems illustrated by a block in the block diagrams may be combined or share hardware and/or software with another one or more of the systems illustrated by a block in the block diagrams. Likewise, a device, system, apparatus, and/or the like may be made up of one or more devices, systems, apparatuses, and/or the like. For example, where a processor is illustrated or described herein, the processor may be made up of a plurality of microprocessors or other processing devices which may or may not be coupled to one another. Likewise, where a memory is illustrated or described herein, the memory may be made up of a plurality of memory devices which may or may not be coupled to one another.

It will also be understood that the one or more computer-executable program code portions may be stored in a transitory or non-transitory computer-readable medium (e.g., a memory, and the like) that can direct a computer and/or other programmable data processing apparatus to function in a particular manner, such that the computer-executable program code portions stored in the computer-readable medium produce an article of manufacture, including instruction mechanisms which implement the steps and/or functions specified in the flowchart(s) and/or block diagram block(s).

The one or more computer-executable program code portions may also be loaded onto a computer and/or other programmable data processing apparatus to cause a series of operational steps to be performed on the computer and/or other programmable apparatus. In some embodiments, this produces a computer-implemented process such that the one or more computer-executable program code portions which execute on the computer and/or other programmable apparatus provide operational steps to implement the steps specified in the flowchart(s) and/or the functions specified in the block diagram block(s). Alternatively, computer-implemented steps may be combined with operator and/or human-implemented steps in order to carry out an embodiment of the present invention.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

What is claimed is:

1. A system for transformation of data structures to maintain data attribute equivalency in diagnostic databases, wherein the system performs transforming and mapping data structures and associated type of coding, across a plurality of distinct databases while still maintaining compatibility, wherein the system performs adapted data transformation by integrating an auxiliary feature data structure within the transformation, the system comprising:

a first database, wherein the first database comprises a plurality of source data structures associated with a first coding type;

a second database, wherein the second database comprises a plurality of target data structures associated with a second coding type;

a computer apparatus including at least one processor, at least one memory device with computer-readable program code stored thereon and a network communication device; and the at least one processor being operatively coupled to the least one memory device and the network communication device, wherein the at least one processor is configured to execute the computer-readable program code to:

receive a feature data structure, wherein the feature data structure comprises user information associated with a first user;

based on at least the user information, determine a first source data structure of the plurality of source data structures of the first database, wherein the first source data structure comprises the first coding type;

determine one or more source attributes associated with the first source data structure;

transform the first source data structure to a first target data structure of the plurality of target data structures of the second database such that (i) the first target data structure comprises the second coding type, and (ii) one or more target attributes associated with the first target data structure are equivalent to the one or more source attributes associated with the first source data structure, wherein transforming the first source data structure to the plurality of target data structures further comprises:

determining one or more probable target data structures of the plurality of target data structures of the second database associated with the first source data structure;

constructing a target transformation mapping structure based on combining a first data structure associated with probability of a class within a corpus, a second data structure associated with probability of a document within the corpus, and a third data structure associated with probability of the document within the class, associated with each of the one or more probable target data structures of the plurality of target data structures;

constructing a plurality of feature weight vectors associated with the target transformation mapping structure;

implementing an iterative gradient descent modification of the plurality of feature weight vectors, wherein the iterative gradient descent modification comprises a modification to the plurality of feature weight vectors at a plurality of iterations, and wherein modification of the feature weight vectors is based on previous modified weights from a preceding iteration of the iterative gradient descent modification;
ending the iterative gradient descent modification of the plurality of feature weight vectors in response to determining that variation in error terms between a current iteration and the preceding iteration is outside a threshold range;
determining an auxiliary data structure associated with the user information associated with the first user; and
integrating the auxiliary data structure with the transformed first source data structure; and
initiate, via a user interface, a presentation of the first target data structure on a display device associated with a user device.

2. The system of claim 1, wherein the first coding type is an ICD-10 based code and the second coding type is an ICD-9 based code.

3. The system of claim 1, wherein the at least one processor is further configured to execute the computer-readable program code to:
retrieve visit information associated with the first user, wherein visit information comprises one or more patient attributes,
wherein the one or more probable target data structures of the plurality of target data structures of the second database associated with the first source data structure are determined based on at least the visit information and the user information, wherein each of the one or more probable target data structures comprise the second coding type, and
wherein the one or more probable target data structures are determined based on determining an inpatient principal diagnosis code, an inpatient other ICD code, an outpatient principal diagnosis code and/or an outpatient other diagnosis code.

4. The system of claim 1, wherein the at least one processor is further configured to execute the computer-readable program code to:
retrieve visit information associated with the first user,
wherein the one or more probable target data structures of the plurality of target data structures of the second database associated with the first source data structure are determined based on at least the visit information and the user information, wherein each of the one or more probable target data structures comprise the second coding type, wherein the one or more probable target data structures comprise the first target data structure; and
determine, for each of the one or more probable target data structures, a probability of class for the first source data structure,
wherein transforming the first source data structure to the first target data structure comprises mapping the first source data structure to the first target data structure of the one or more probable target data structures based on determining that the first target data structure comprises a highest probability of class.

5. The system of claim 4, wherein the visit information comprises one or more patient attributes selected from a group comprising a patient type, a patient class, a point of origin, an admit type, a discharge status and/or MS-DRG data, wherein the at least one processor is further configured to execute the computer-readable program code to construct arguments of maxima associated with the target transformation mapping structure.

6. The system of claim 1, wherein the first source data structure is associated with a first ICD code of the first coding type, wherein one or more source attributes comprise an ICD type, an ICD class, a rank and/or a Present on Admission (POA) indicator, wherein the at least one processor is further configured to execute the computer-readable program code to implement Laplace smoothing over at least a component of the target transformation mapping structure.

7. The system of claim 1, wherein the first target data structure is associated with a first ICD code of the second coding type, wherein one or more target attributes comprise an ICD type, an ICD class, a rank and/or a Present on Admission (POA) indicator, wherein the at least one processor is further configured to execute the computer-readable program code to implement facility stratification over at least a component of the target transformation mapping structure.

8. The system of claim 1, wherein the at least one processor is further configured to execute the computer-readable program code to:
determine whether a discharge patient attribute associated with the first user succeeds a predetermined time interval; and
transform the first source data structure to the first target data structure based on at least determining that the discharge patient attribute associated with the first user succeeds a predetermined time interval.

9. The system of claim 1, wherein the at least one processor is further configured to execute the computer-readable program code to:
determine whether a discharge patient attribute associated with a second user succeeds a predetermined time interval; and
retrieve a second target data structure of the plurality of target data structures of the second database, based on at least determining that the discharge patient attribute associated with the first user precedes a predetermined time interval.

10. A computer program product for transformation of data structures to maintain data attribute equivalency in diagnostic databases, wherein the computer program product performs transforming and mapping data structures and associated type of coding, across a plurality of distinct databases while still maintaining compatibility, wherein the computer program product performs adapted data transformation by integrating an auxiliary feature data structure within the transformation, the computer program product comprising a non-transitory computer-readable storage medium having computer-executable instructions to:
receive a feature data structure, wherein the feature data structure comprises user information associated with a first user;
based on at least the user information, determine a first source data structure of a plurality of source data structures of a first database, wherein the first source data structure comprises a first coding type;
determine one or more source attributes associated with the first source data structure; transform the first source data structure to a first target data structure of a plurality of target data structures of a second database such that (i) the first target data structure comprises a second coding type, and (ii) one or more target attributes associated with the first target data structure are equivalent to the one or more source attributes associated with the first source data structure, wherein transforming the first source data structure to the plurality of target data structures further comprises:
  determining one or more probable target data structures of the plurality of target data structures of the second database associated with the first source data structure;
  constructing a target transformation mapping structure based on combining a first data structure associated with probability of a class within a corpus, a second data structure associated with probability of a document within the corpus, and a third data structure associated with probability of the document within the class, associated with each of the one or more probable target data structures of the plurality of target data structures;
  constructing a plurality of feature weight vectors associated with the target transformation mapping structure;
  implementing an iterative gradient descent modification of the plurality of feature weight vectors, wherein the iterative gradient descent modification comprises a modification to the plurality of feature weight vectors at a plurality of iterations, and wherein modification of the feature weight vectors is based on previous modified weights from a preceding iteration of the iterative gradient descent modification;
  ending the iterative gradient descent modification of the plurality of feature weight vectors in response to determining that variation in error terms between a current iteration and the preceding iteration is outside a threshold range;
  determining an auxiliary data structure associated with the user information associated with the first user; and
  integrating the auxiliary data structure with the transformed first source data structure; and
  initiate, via a user interface, a presentation of the first target data structure on a display device associated with a user device.

11. The computer program product of claim 10, wherein the first coding type is an ICD-10 based code and the second coding type is an ICD-9 based code.

12. The computer program product of claim 10, wherein the non-transitory computer-readable storage medium further has computer-executable instructions to:
  retrieve visit information associated with the first user, wherein visit information comprises one or more patient attributes; and
  wherein the determine-one or more probable target data structures of the plurality of target data structures of the second database associated with the first source data structure are determined based on at least the visit information and the user information, wherein each of the one or more probable target data structures comprise the second coding type, and
  wherein the one or more probable target data structures are determined based on determining an inpatient principal diagnosis code, an inpatient other ICD code, an outpatient principal diagnosis code and/or an outpatient other diagnosis code.

13. The computer program product of claim 10, wherein the non-transitory computer-readable storage medium further has computer-executable instructions to: retrieve visit information associated with the first user, wherein the one or more probable target data structures of the plurality of target data structures of the second database associated with the first source data structure are determined based on at least the visit information and the user information, wherein each of the one or more probable target data structures comprise the second coding type, wherein the one or more probable target data structures comprise the first target data structure; and
  determine, for each of the one or more probable target data structures, a probability of class for the first source data structure,
  wherein transforming the first source data structure to the first target data structure comprises mapping the first source data structure to the first target data structure of the one or more probable target data structures based on determining that the first target data structure comprises a highest probability of class.

14. The computer program product of claim 13, wherein the visit information comprises one or more patient attributes selected from a group comprising a patient type, a patient class, a point of origin, an admit type, a discharge status and/or MS-DRG data.

15. The computer program product of claim 10, wherein the first source data structure is associated with a first ICD code of the first coding type, wherein one or more source attributes comprise an ICD type, an ICD class, a rank and/or a Present on Admission (POA) indicator.

16. A computerized method for transformation of data structures to maintain data attribute equivalency in diagnostic databases, wherein the computerized method is performs transforming and mapping data structures and associated type of coding, across a plurality of distinct databases while still maintaining compatibility, wherein the computerized method performs adapted data transformation by integrating an auxiliary feature data structure within the transformation, the computerized method comprising:
  receiving a feature data structure, wherein the feature data structure comprises user information associated with a first user;
  based on at least the user information, determining a first source data structure of a plurality of source data structures of a first database, wherein the first source data structure comprises a first coding type;
  determining one or more source attributes associated with the first source data structure; transforming the first source data structure to a first target data structure of a plurality of target data structures of a second database such that (i) the first target data structure comprises a second coding type, and (ii) one or more target attributes associated with the first target data structure are equivalent to the one or more source attributes associated with the first source data structure, wherein transforming the first source data structure to the plurality of target data structures further comprises:
    determining one or more probable target data structures of the plurality of target data structures of the second database associated with the first source data structure;
    constructing a target transformation mapping structure based on combining a first data structure associated with probability of a class within a corpus, a second data structure associated with probability of a document within the corpus, and a third data structure associated with probability of the document within the class, associated with each of the one or more probable target data structures of the plurality of target data structures;

constructing a plurality of feature weight vectors associated with the target transformation mapping structure;

implementing an iterative gradient descent modification of the plurality of feature weight vectors, wherein the iterative gradient descent modification comprises a modification to the plurality of feature weight vectors at a plurality of iterations, and wherein modification of the feature weight vectors is based on previous modified weights from a preceding iteration of the iterative gradient descent modification;

ending the iterative gradient descent modification of the plurality of feature weight vectors in response to determining that variation in error terms between a current iteration and the preceding iteration is outside a threshold range;

determining an auxiliary data structure associated with the user information associated with the first user; and integrating the auxiliary data structure with the transformed first source data structure; and initiating, via a user interface, a presentation of the first target data structure on a display device associated with a user device.

17. The computerized method of claim 16, wherein the first coding type is an ICD-10 based code and the second coding type is an ICD-9 based code.

18. The computerized method of claim 16, wherein the computerized method further comprises:

retrieving visit information associated with the first user, wherein visit information comprises one or more patient attributes, wherein the one or more probable target data structures of the plurality of target data structures of the second database associated with the first source data structure are determined based on at least the visit information and the user information, wherein each of the one or more probable target data structures comprise the second coding type, and wherein the one or more probable target data structures are determined based on determining an inpatient principal diagnosis code, an inpatient other ICD code, an outpatient principal diagnosis code and/or an outpatient other diagnosis code.

19. The computerized method of claim 16, wherein the computerized method further comprises:

retrieving visit information associated with the first user, wherein the one or more probable target data structures of the plurality of target data structures of the second database associated with the first source data structure are determined based on at least the visit information and the user information, wherein each of the one or more probable target data structures comprise the second coding type, wherein the one or more probable target data structures comprise the first target data structure; and determining, for each of the one or more probable target data structures, a probability of class for the first source data structure, wherein transforming the first source data structure to the first target data structure comprises mapping the first source data structure to the first target data structure of the one or more probable target data structures based on determining that the first target data structure comprises a highest probability of class.

20. The computerized method of claim 16, wherein the first source data structure is associated with a first ICD code of the first coding type, wherein one or more source attributes comprise an ICD type, an ICD class, a rank and/or a Present on Admission (POA) indicator.

* * * * *